United States Patent [19]

Phan et al.

[11] Patent Number: 5,451,452
[45] Date of Patent: Sep. 19, 1995

[54] ABSORBENT MEMBERS AND ARTICLES CONTAINING SUPERABSORBENT POLYMER FOAM

[75] Inventors: Dean V. Phan, West Chester; Paul D. Trokhan, Hamilton, both of Ohio

[73] Assignee: The Procter & Gamble Company, Cincinnati, Ohio

[21] Appl. No.: 249,510

[22] Filed: May 26, 1994

Related U.S. Application Data

[62] Division of Ser. No. 38,580, Mar. 26, 1993, Pat. No. 5,338,766.

[51] Int. Cl.$^6$ .............................................. B32B 27/00
[52] U.S. Cl. .................. 428/290; 428/315.7; 428/315.9; 428/317.9; 604/369
[58] Field of Search ............... 428/290, 315.7, 315.9, 428/317.9; 604/369

[56] References Cited

U.S. PATENT DOCUMENTS

| | | | |
|---|---|---|---|
| Re. 32,649 | 4/1988 | Brandt et al. | 604/368 |
| 3,878,175 | 4/1975 | Steckler | 521/63 |
| 3,901,240 | 8/1975 | Hoey | 604/364 |
| 3,966,679 | 6/1976 | Gross | 525/107 |
| 4,008,353 | 2/1977 | Gross et al. | 428/522 |
| 4,061,846 | 12/1977 | Gross et al. | 525/119 |
| 4,071,650 | 1/1978 | Gross | 428/260 |
| 4,082,878 | 8/1976 | Boe et al. | 428/290 |

(List continued on next page.)

FOREIGN PATENT DOCUMENTS

| | | |
|---|---|---|
| 0049944 | 4/1982 | European Pat. Off. . |
| 0196364 | 10/1986 | European Pat. Off. . |
| 0257308 | 3/1988 | European Pat. Off. . |
| 0272074 | 6/1988 | European Pat. Off. . |
| 0290814 | 11/1988 | European Pat. Off. . |
| 0293762 | 12/1988 | European Pat. Off. . |
| 0295438 | 12/1988 | European Pat. Off. . |
| 0301804 | 2/1989 | European Pat. Off. . |
| 0304952 | 3/1989 | European Pat. Off. . |
| 0324385 | 7/1989 | European Pat. Off. . |
| 0342919 | 11/1989 | European Pat. Off. . |
| 0347241 | 12/1989 | European Pat. Off. . |
| 0538983A1 | 4/1993 | European Pat. Off. . |
| 2337028 | 7/1977 | France . |
| 52-53546 | 12/1978 | Japan . |
| 55-151034 | 11/1980 | Japan . |
| 55-58738 | 12/1981 | Japan . |
| 63-291908 | 11/1988 | Japan . |
| 5-188972 | 2/1993 | Japan . |
| 1452325 | 10/1976 | United Kingdom . |
| 2136813 | 9/1984 | United Kingdom . |
| WO88/09801 | 12/1988 | WIPO . |
| WO91/02552 | 3/1991 | WIPO . |
| WO91/15362 | 10/1991 | WIPO . |
| WO92/19445 | 11/1992 | WIPO . |
| WO93/00474 | 1/1993 | WIPO . |
| WO93/00475 | 1/1993 | WIPO . |

OTHER PUBLICATIONS

*Trademarks of ICI Americas, Inc.,* Chapters 1–8, ICI Americas, Inc. 1984.
Weber et al., "New Melamine-based Elastic Foam," Kunststoffe 75 (1985) 11, pp. 843–848.
*Carbopol Water Soluble Resins,* B.F. Goodrich, technical brochure.

*Primary Examiner*—Morton Foelak
*Attorney, Agent, or Firm*—Loretta J. Henderson; Bart S. Hersko; Steven W. Miller

[57] ABSTRACT

An improved superabsorbent polymer foam having a morphology to provide improved absorptive properties is disclosed. The foam preferably comprises a superabsorbent polymer formed from a substantially water-soluble, unsaturated monomer having neutralized carboxyl groups and a substantially water-soluble internal crosslinking agent. The monomer and crosslinking agent are expanded in the presence of a substantially water-insoluble blowing agent and a suitable solvent and reacted to form a superabsorbent polymer foam having substantially continuous, intercommunicating channels substantially throughout the foam and a relatively high surface area to mass ratio.

Methods for making the foam and absorbent products, members and articles containing the foam are also disclosed.

12 Claims, 4 Drawing Sheets

U.S. PATENT DOCUMENTS

| | | | |
|---|---|---|---|
| 4,117,184 | 9/1978 | Erickson et al. | 428/224 |
| 4,235,237 | 11/1980 | Mesek et al. | 604/368 |
| 4,293,600 | 10/1978 | Fink et al. | 427/385.5 |
| 4,354,487 | 10/1982 | Oczkowski et al. | 604/366 |
| 4,378,278 | 3/1983 | Allaway et al. | 521/50.5 |
| 4,394,930 | 7/1983 | Korpman | 220/444 |
| 4,410,571 | 10/1983 | Korpman | 521/88 |
| 4,415,388 | 11/1983 | Korpman | 156/78 |
| 4,449,977 | 5/1984 | Korpman | 604/366 |
| 4,493,920 | 1/1985 | Le-Khac | 525/67 |
| 4,522,953 | 6/1985 | Baxby et al. | 521/64 |
| 4,529,739 | 7/1985 | Scott et al. | 521/72 |
| 4,535,098 | 8/1985 | Evani et al. | 521/149 |
| 4,540,717 | 9/1985 | Mahnke et al. | 521/52 |
| 4,605,700 | 8/1986 | Le-Khac | 525/73 |
| 4,612,334 | 9/1986 | Jones et al. | 521/64 |
| 4,616,063 | 10/1986 | Le-Khac | 525/91 |
| 4,618,631 | 10/1986 | Takeda et al. | 521/109.1 |
| 4,649,164 | 3/1987 | Scott et al. | 521/149 |
| 4,705,773 | 11/1987 | Le-Khac | 502/402 |
| 4,725,628 | 2/1988 | Garvey et al. | 521/137 |
| 4,725,629 | 2/1988 | Garvey et al. | 521/137 |
| 4,731,067 | 3/1988 | Le-Khac | 604/367 |
| 4,731,391 | 3/1988 | Garvey | 521/137 |
| 4,740,528 | 4/1988 | Garvey et al. | 521/128 |
| 4,748,076 | 5/1988 | Saotome | 428/224 |
| 4,749,746 | 6/1988 | Dean et al. | 525/67 |
| 4,808,637 | 2/1989 | Boardman et al. | 521/50.5 |
| 4,813,945 | 3/1989 | Le-Khac | 604/367 |
| 4,861,539 | 8/1989 | Allen et al. | 604/376 |
| 4,880,868 | 11/1989 | Le-Khac | 264/204 |
| 4,888,238 | 12/1989 | Katz et al. | 604/371 |
| 4,948,818 | 8/1990 | Carmody et al. | 521/149 |
| 4,985,467 | 1/1991 | Kelly et al. | 521/52 |
| 4,990,541 | 2/1991 | Nielson et al. | 521/70 |
| 5,071,681 | 12/1991 | Manning et al.4 | 427/392 |
| 5,079,034 | 11/1988 | Miyake et al. | 427/521 |
| 5,102,597 | 4/1992 | Roe et al. | 264/126 |
| 5,118,719 | 7/1994 | Lind | 521/64 |
| 5,124,188 | 6/1992 | Roe et al. | 428/72 |
| 5,141,794 | 8/1992 | Arroyo | 428/138 |
| 5,147,344 | 9/1992 | Sachau et al. | 604/368 |
| 5,147,345 | 9/1992 | Young et al. | 604/378 |
| 5,149,720 | 9/1992 | DesMarais et al. | 521/63 |
| 5,154,713 | 10/1992 | Lind | 521/92 |
| 5,171,237 | 12/1992 | Poccia et al. | 604/379 |
| 5,175,046 | 12/1992 | Nguyen | 428/198 |
| 5,189,070 | 2/1993 | Brownscombe et al. | 521/64 |
| 5,198,472 | 12/1992 | DesMarais et al. | 521/63 |
| 5,210,104 | 5/1993 | Bast | 521/64 |
| 5,250,576 | 10/1993 | DesMarais et al. | 521/63 |
| 5,260,345 | 11/1993 | DesMarais et al. | 521/148 |
| 5,268,224 | 12/1993 | DesMarais et al. | 428/286 |
| 5,292,777 | 3/1994 | DesMarais et al. | |
| 5,318,554 | 6/1994 | Young et al. | |

ABSORBENT MEMBERS AND ARTICLES CONTAINING SUPERABSORBENT POLYMER FOAM

This is a divisional of application Ser. No. 08/038,580, filed on Mar. 26, 1993, now U.S. Pat. No. 5,338,766.

BACKGROUND OF THE INVENTION

A) FIELD OF THE INVENTION

The present invention relates to superabsorbent polymer foams and, more particularly, to an improved superabsorbent polymer foam having a morphology which provides improved absorptive properties, e.g., substantially continuous intercommunicating channels substantially throughout the foam and a relatively high surface area to mass ratio. The superabsorbent polymer foams of the present invention are especially useful in absorbent members which can be incorporated into absorbent articles such as diapers, adult incontinence pads, sanitary napkins, and the like. The present invention also relates to methods for producing such a superabsorbent polymer foam.

B) BACKGROUND INFORMATION

"Superabsorbent" polymer materials (also known as hydrogels, hydrocolloids, osmetics and absorbent gelling materials) are generally capable Of absorbing large quantities of fluids such as water and body exudates and are further capable of retaining such absorbed fluids under moderate pressures. These absorptive characteristics make such materials especially useful for incorporation into absorbent articles such as diapers, sanitary napkins, and the like.

The art teaches superabsorbent foams formed of superabsorbent polymer material. For example, U.S. Pat. No. 4,529,739 issued to Scott et al. on Jul. 16, 1985 and U.S. Pat. No. 4,649,164 issued to Scott et al. on Mar. 10, 1987, teach a foamed, water-swellable, polymeric water absorbent material prepared by contacting a polymer capable of having a water-swellable character and containing acid moieties in acid form with a blowing agent capable of neutralizing the acid moieties. U.S. Pat. No. 4,808,637 issued to Boardman et al. on Feb. 28, 1989 and European Patent Application No. 0295438 published by Boardman on Dec. 21, 1988, teach an acrylate superabsorbent composition having an improved rate of absorbency, low residual acid content and a low acrylate monomer content, formed by uniformly reacting a mixture of acrylic acid, an alkali metal salt of carbonic acid, aluminum acetate, sodium persulfate and water using a microwave heat source. U.S. Pat. No. 5,154,713 issued to Lind on Oct. 13, 1992, teaches a superabsorbent polymer having an increased rate of water absorption obtained by the addition, preferably prior to polymerization, of a carbonate blowing agent to a monomer solution of the monomers used to form the superabsorbent polymer.

The art also teaches foams containing particulate, non-foamed superabsorbent materials. See, for example, U.S. Pat. No. 4,394,930 issued to Korpman on Jul. 26, 1983; U.S. Pat. No. 4,415,388 issued to Korpman on Nov. 15, 1983; and Great Britain Patent Application 2136813A published by Korpman on Sep. 26, 1984. These references teach foam products prepared from solid, particulate superabsorbent polymer, a blowing agent, and a liquid polyhydroxy compound. U.S. Pat. No. 4,725,629 issued to Garvey et al. on Feb. 16, 1988, teaches a superabsorbent polyurethane foam based on an interpenetrating polymer network of a crosslinked polyurethane and crosslinked addition polymer, prepared by forming the polyurethane foam in the presence of addition polymerizable monomers, a crosslinking agent and a free radical initiator.

While the above foams may be useful absorbent materials, they have not shown to be optimal for use in disposable products because their absorptive properties tend to be limited. The superabsorbent foams formed of superabsorbent material tend to be characterized by discontinuous channels. Such foams tend to possess a relatively large average cell size and wide cell size distribution, i.e., the foams have a relatively large diameter capillary structure in which the capillary diameter varies widely and randomly. It is believed that the large average cell size and discontinuous channels result in a foam product having a relatively low surface area to mass ratio such that the osmotic absorptive rate is not optimal. In addition, it is believed that the discontinuity of foam channels and a wide cell size distribution limit the ability of fluids to flow by capillary transport through the foam structure. This limitation of the capillary transport properties is believed to limit both the osmotic and capillary absorptive properties of such foams, more particularly the capillary absorptive capacity and rate and the osmotic absorptive rate. Thus, the absorptive rates and capacities of such foam products tend to be limited.

In a composition in which particulate superabsorbent polymer materials are present in a foam made of non-superabsorbent material such as polyurethane, the foamed portion of the composition is not superabsorbent as defined herein since it does not have sufficient ability to retain absorbed fluids. Therefore, although the superabsorbent particulate portion of the structure may be able to retain fluids, the overall capacity of the foam to absorb and retain fluids is limited. Further, the overall absorptive properties of the foam tend to be limited due to the relatively low surface area to mass ratio of the particulate portion relative to the foam portion. This is believed to be particularly important for absorption of body fluids containing high molecular weight components, e.g., blood and menses. Such components are believed to deactivate particulate superabsorbent materials due to their large molecular size relative to the particulate material. The high molecular weight components may also deactivate regions of a foam characterized by a discontinuous channel. In addition, the use of polyurethane materials in applications intended for human contact such as diapers presents concerns over the potential toxicity of materials that may be used to prepare the polyurethane.

Thus, there is a continuing need in the field of superabsorbent materials to provide materials having faster absorptive rates and greater absorptive capacities. More particularly, there is a need to provide absorbent articles having such improved absorptive properties while reducing the overall thickness of the absorbent article. For absorbent articles, it is desirable to use materials which are non-toxic to humans. Additionally, it is desirable to provide such materials and absorbent articles in a cost-effective manner, e.g., by rapid, simple and safe manufacturing techniques.

It is therefore an object of the present invention to provide a superabsorbent polymer foam having an improved absorptive rate and improved fluid distribution properties. An additional object of the present invention is to provide a superabsorbent polymer foam having a morphology which provides an increased absorptive rate, particularly characterized by a high surface area to mass ratio. Another object of the present invention is to provide such a superabsorbent polymer foam which does not present undesirable risks to human health. In addition, it is an object of the present invention to provide a cost-effective method of making such foams.

An additional object of the present invention is to provide absorbent products, members and articles having improved absorptive rates. Another object of the present invention is to provide absorbent members whose absorptive properties are tailored to the requirements of their intended application. An additional object of the present invention is to minimize the thickness of absorbent articles while providing improved absorptive properties.

SUMMARY OF THE INVENTION

The present invention relates to a superabsorbent polymer foam comprising superabsorbent polymer material. In a preferred embodiment, the superabsorbent polymer material of the foam is formed from a substantially water-soluble, unsaturated monomer comprising neutralized carboxyl groups reacted with a substantially water-soluble internal crosslinking agent. In a preferred embodiment, the monomer and internal crosslinking agent are expanded in the presence of a blowing agent and a solvent so as to form an expanded structure, the solvent being a solvent for the monomer and internal crosslinking agent but not for the blowing agent or the superabsorbent polymer material (preferably water). The expanded structure is subjected to conditions so as to react the monomer and internal crosslinking agent to form the superabsorbent polymer material. The expansion and reaction are controlled such that the resultant superabsorbent polymer foam has a morphology which provides an improved absorptive rate, which may be characterized by substantially continuous intercommunicating channels substantially throughout the foam and a relatively high surface area to mass ratio, small average cell size, and low density.

It is believed that the superabsorbent polymer foams of the present invention have improved absorptive rates and capacities relative to known superabsorbent foams. It has been found that when a foam of the present invention is contacted with fluids, the foam swells generally isotropically even under moderate confining pressures, absorbs and transports such fluids into and within the intercommunicating channels, and imbibes such fluids into the superabsorbent polymer material of the foam, where they are retained. Since the foam has substantially continuous intercommunicating channels substantially throughout the foam structure, it tends to rapidly absorb fluids by substantially unrestricted capillary transport, particularly in the vertical direction. In addition, since the intercommunicating channels allow distribution of fluids throughout the foam, they provide increased utilization of the fluid-retentive (osmotic absorptive) properties of the polymer making up the foam. Once saturated to its osmotic absorptive capacity, it is believed that the intercommunicating channels of the foams herein provide improved capillary absorptive capacity. The foams of the present invention have a relatively high surface area to mass ratio which enhances the osmotic absorptive rate of the polymer material. Thus, the overall absorptive rate and capacity of the foam tends to be maximized.

The morphology of the foams of the present invention may also minimize deactivation of the superabsorbent material of the foam by high molecular weight fluids. In addition, the present foams tend to possess greater flexibility as compared to known foams formed of superabsorbent polymer material. Additionally, the superabsorbent polymer foams of the present invention do not present the undesirable risks to human health that may be present in some known superabsorbent foams.

The invention also relates to improved absorbent products, absorbent members and absorbent articles incorporating the superabsorbent polymer foams of the present invention. It is believed that the foams enhance the fluid handling characteristics of such items by rapidly acquiring fluids and efficiently distributing and storing such fluids, thereby allowing for the acquisition and transport of subsequent loadings of fluids. As a result, the overall absorptive rate and capacity of such products, members and articles is increased.

The present invention also relates to methods of making the superabsorbent polymer foams. In a preferred embodiment, the foam is prepared by:

(I) forming a reaction mixture comprising the monomer, internal crosslinking agent, and solvent;

(II) dispersing a blowing agent in the reaction mixture;

(III) stabilizing the dispersion of the blowing agent in the reaction mixture;

(IV) expanding the blowing agent;

(V) reacting the monomer and internal crosslinking agent so as to form a superabsorbent polymer material; and (VI) controlling the dispersion, stabilization, expansion, and reaction steps such that the resultant superabsorbent polymer foam has a morphology which provides an improved absorptive rate and fluid distribution properties.

BRIEF DESCRIPTION OF THE DRAWINGS

While the specification concludes with claims particularly pointing out and distinctly claiming the present invention, it is believed that the present invention will be better understood from the following description in conjunction with the accompanying drawings in which:

DETAILED DESCRIPTION OF THE INVENTION

Figure 1:
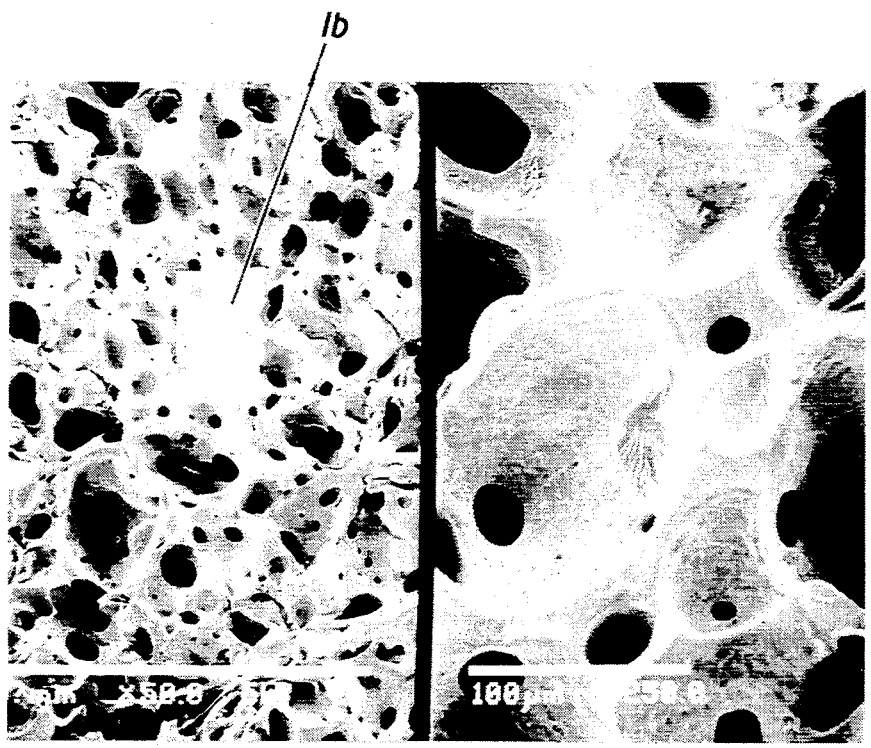
FIG. 1 is a photomicrograph showing a top view of an edge of a superabsorbent polymer foam of the present invention enlarged approximately 50 times and also a portion of this view enlarged approximately 250 times.

The superabsorbent polymer foams of the present invention are capable of absorbing large quantities of fluids (i.e., liquids) such as water and/or body exudates (e.g., urine or menses) and are further capable of retaining such fluids under moderate pressures, such as those encountered in the wearing of absorbent articles. The foams are formed of superabsorbent polymer material, commonly referred to as hydrogel, hydrocolloid, osmotic and absorbent gelling material. As used herein, "superabsorbent polymer" means a substantially water-insoluble, slightly crosslinked, partially neutralized, hydrogel-forming polymer material which is capable of absorbing and retaining large quantities of fluids such as water and/or body exudates. Superabsorbent polymer materials typically have the ability to absorb and retain, under moderate pressures, such fluids in an amount of at least about 10 times, preferably at least about 15 times, most preferably at least about 50 times, the dry weight of the polymer material. By "polymer foam" is meant the structure which results when a relatively monomer-free gas or relatively monomer-free liquid is dispersed as bubbles in a liquid containing polymerizable, superabsorbent-polymer-forming reactants, followed by expansion of the bubbles and polymerization of the reactants in the liquid which surrounds the expanded bubbles. The resultant polymerized, expanded structure can be in the form of a porous solidified structure which is an aggregate of cells, the boundaries or walls of which cells comprise solid polymerized material. After expansion and polymerization, the cells themselves are typically free of the relatively monomer free gas or liquid which, prior to expansion and polymerization, had formed the bubbles in the liquid dispersion.

In its broadest aspect, the superabsorbent polymer foams of the present invention comprise a superabsorbent polymer material formed from a reaction mixture comprising (i) superabsorbent-polymer-forming reactants which are capable of being made substantially soluble in a solvent and (ii) such solvent. A blowing agent is dispersed in the reaction mixture, stabilized, and expanded so as to form an expanded structure. During or after formation of the expanded structure, the superabsorbent-polymer-forming reactants are reacted so as to form a polymer material which is substantially insoluble in the solvent. (The polymer material may or may not be superabsorbent by the time the reaction has advanced to the point of insoluble polymer formation. If not superabsorbent at that point, the polymer is further reacted in order to render it superabsorbent.) The dispersion, stabilization, expansion, and reaction steps are controlled such that the resultant polymer foam has a morphology to provide improved absorptive properties, which morphology may be characterized by substantially continuous intercommunicating channels substantially throughout the foam and a relatively high surface area to mass ratio.

A "dispersion of the blowing agent" in the reaction mixture means that the blowing agent is present in the form of discrete particles in the reaction mixture, the blowing agent particles being relatively free of superabsorbent-polymer-forming reactants and solvent. By "substantially soluble" it is meant that the superabsorbent-polymer-forming reactant (or other component so described) may be dissolved or dispersed in the solvent such that a minimum defined level of the reactant (or component) is extractable from the solvent. Substantially soluble reactants or components are those which can be dissolved or dispersed in the solvent such that at least about 50%, preferably at least about 60%, more preferably at least about 75%, most preferably at least about 80%, of the reactant or component which was dissolved or dispersed in the solvent is extractable. "Substantially insoluble" means that a reactant, component, reaction product, or other material (including the superabsorbent polymer material of the superabsorbent polymer foam) so described can be dissolved or dispersed in the solvent such that less than about 50%, preferably less than about 40%, more preferably less than about 25%, most preferably less than about 20%, of such reactant, component, reaction product or other material which was dissolved or dispersed in the solvent is extractable. A suitable method for determining extractable levels is described in the TEST METHODS section. Typically, the substantially insoluble polymer materials formed herein possess a relatively high weight average molecular weight, e.g., of at least about 200,000 grams/mole. Such a high molecular weight is a typical characteristic of network crosslinked polymers having a certain degree of network crosslinking. In contrast, "substantially soluble polymers" are typically substantially linear, i.e., the polymer molecule is generally two-dimensional with no or only a minimal degree of crosslinking.

In a preferred embodiment, the superabsorbent polymer foam comprises a superabsorbent polymer material formed from:

(I) a substantially water-soluble, unsaturated monomer comprising neutralized carboxyl groups; and (II) a substantially water-soluble internal crosslinking agent reacted with the monomer.

The preferred superabsorbent polymer foam is preferably formed by first forming a reaction mixture comprising the monomer, the internal crosslinking agent, and a suitable solvent (preferably water). A blowing agent is then stably dispersed in the reaction mixture, followed by expansion of the blowing agent and reaction of the monomer and the internal crosslinking agent so as to form a foam comprised of a substantially water-insoluble polymer material. (Depending on the reactant type and conditions, the insoluble polymer material may or may not be superabsorbent and may therefore require further reaction, e.g., neutralization of carboxyl groups and/or further crosslinking of the polymer material to render it superabsorbent.) The dispersion, stabilization, expansion, and reaction steps are controlled such that the foam has a morphology which may be characterized by intercommunicating channels and a relatively high surface area to mass ratio.

Formation of the Reaction Mixture

One component of the preferred reaction mixture is a substantially water-soluble monomer comprising neutralized or neutralizable carboxyl groups. The monomer preferably contains sufficient carboxyl groups such that a linear polymer thereof is substantially water-soluble (i.e., the carboxyl groups are hydrophilic). Mixtures of such monomers may also be used.

The monomers comprising carboxyl groups include acid, acid anhydride, and ester group containing monomers. These monomers may also contain other hydrophilic groups, such as hydroxyl groups, amide-groups, amino groups, nitrile groups, and quaternary ammonium salt groups. Preferably, the monomer contains acid type hydrophilic groups. More preferably, the monomer contains at least about 5 mole percent, most preferably at least about 10 mole percent, of acid groups.

Monomers containing carboxyl groups include the olefinically unsaturated acids, esters thereof, and anhydrides which contain at least one carbon to carbon olefinic double bond. More specifically, these monomers can be selected from olefinically unsaturated carboxylic acids, esters of such carboxylic acids, acid anhydrides, sulfonic acids, esters of such sulfonic acids, and mixtures of any two or more of the foregoing monomers.

Olefinically unsaturated carboxylic acid and carboxylic acid anhydride monomers include the acrylic acids and derivatives thereof, typified by acrylic acid itself, methacrylic acid, ethacrylic acid, alpha-chloroacrylic acid, alpha-cyano acrylic acid, beta-methyl acrylic acid (i.e., crotonic acid), alpha-phenyl acrylic acid, beta-acryloxy propionic acid, and beta-steryl acrylic acid; maleic acid; and maleic acid anhydride. Other monomers of this type are sorbic acid, alpha-chloro sorbic acid, angelic acid, cinnamic acid, p-chloro cinnamic acid, itaconic acid, citraconic acid, mesaconic acid, glutaconic acid, aconitic acid, fumaric acid, and tricarboxyethylene.

Olefinically unsaturated sulfonic acid monomers and derivatives thereof include aliphatic or aromatic vinyl sulfonic acids such as vinylsulfonic acid, allyl sulfonic acid, vinyltoluene sulfonic acid and styrene sulfonic acid; and acrylic and methacrylic sulfonic acid derivatives such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-methyl propane sulfonic acid.

The carboxyl groups (e.g., acid groups) are at least partially neutralized with cations capable of forming a salt with the monomer to form a monomer having neutralized carboxyl groups. Such salt-forming cations include, for example, alkali or alkaline metals, ammonium, substituted ammonium and amines as discussed in further detail in U.S. Pat. No. Re. 32,649, Brandt et al., Apr. 19, 1988, incorporated herein by reference. Neutralization is preferably carried out in any conventional manner which results in at least about 25 mole percent, more preferably at least about 50 mole percent, most preferably at least about 75 mole percent, of the total carboxyl groups being neutralized. The carboxyl groups are preferably neutralized prior to formation of the substantially water-insoluble polymer foam, e.g., neutralization is preferably carried out on the monomer or of a water-soluble polymer thereof.

Monomers possessing hydrophilic groups other than carboxyl groups may be used with the carboxyl group containing monomer. Other hydrophilic groups include hydroxyl groups, amide-groups, amino groups, nitrile groups, and quaternary ammonium salt groups. Monomers containing such groups are well known materials and are described in greater detail, for example, in U.S. Pat. No. 4,076,663 issued to Masuda et al. on Feb. 28, 1978; and U.S. Pat. No. 4,062,817 issued to Westerman on Dec. 13, 1977; which patents are incorporated herein by reference. One or more types of such hydrophilic groups may be present in the monomer.

Although this disclosure is generally in terms of the monomer, it is to be understood that substantially water-soluble homopolymers, copolymers, or reaction products of the monomer may also be used in place of or in addition to the toohomer form. Such alternative starting materials include substantially water-soluble homopolymers of the toohomer and substantially water-soluble reaction products of the monomer or its homopolymer and the internal crosslinking agent. For example, a substantially linear, substantially water-soluble homopolymer can be formed by subjecting the monomer to known polymerization conditions. A substantially water-soluble, partially crosslinked polymer may also be formed by reacting (e.g., by heating) the monomer or linear polymer thereof with a crosslinking agent such as the internal crosslinking agents herein. Such a polymer would typically have a low level of crosslinking, e.g., less than about 5%.

The above polymers of the monomer (especially a linear polymer of the monomer) may be preferred starting materials in order to control the viscosity of the reaction mixture so as to aid formation of a foam having a desired morphology, particularly a relatively small cell size. In general, a reaction mixture using such polymers will have a higher viscosity compared to a reaction mixture starting with the toohomer itself. Use of such polymers may also be particularly useful where foams having a low residual monomer content are desired, since residual monomer which may be present in the polymer of the monomer (e.g., a linear polymer of the monomer) may be removed by known processes, e.g., flashing, prior to use in the reaction mixture.

The preferred reaction mixture additionally comprises a substantially water-soluble internal crosslinking agent. Suitable internal crosslinking agents are compounds which are capable of reacting with the monomer to form a substantially water-insoluble, preferably superabsorbent, polymer material. Preferably, the internal crosslinking agent will be such that the reaction mixture has an activation temperature which is greater than the vaporization temperature of the blowing agent and the critical temperature. The activation temperature is the temperature, for a given reaction mixture, at which the internal crosslinking agent will react with the monomer to form a high molecular weight, network crosslinked polymer. The activation temperature can be determined by differential scanning calorimetry (i.e., DSC). DSC techniques are generally described in *Analytical Calorimetry*, Vol. 3, Roger S. Porter et al., Plenum Press (1974), pages 17–44, incorporated herein by reference. Suitable DSC equipment includes the Perkin-Elmer DSC 7 Series Thermal Analysis System, available from Perkin-Elmer of Norwalk, Conn. A suitable method for determining the activation temperature is described in the manual *Perkin-Elmer 7 Series Thermal Analysis System*, Perkin-Elmer, Jan. 1990, incorporated herein by reference.

Suitable internal crosslinking agents include compounds having at least two polymerizable double bonds; compounds having at least one polymerizable double bond and at least one functional group reactive with the monomer; compounds having at least two functional groups reactive with the monomer; and polyvalent metal compounds which can form ionic linkages. One or more internal crosslinking agents may be used. Typical internal crosslinking agents are described in greater detail in the above cited U.S. Pat. No. 4,076,663. Selection of a particular internal crosslinking agent is determined in part by the desired rate of reaction of the internal crosslinking agent with the monomer at a particular temperature, which rate can be readily determined by one having ordinary skill in the art. The internal crosslinking agent is preferably selected from the group consisting of N,N'-methylenebisacrylamide, triallylamine, triallylphosphate, and di- or poly- glycidyl ethers of aliphatic polyvalent alcohols. Most preferably, N,N'-methylenebisacrylamide is used.

The internal crosslinking agent will typically be present in the reaction mixture in an amount of from about 0.001 mole percent to about 5 mole percent based on the total moles of monomer present in the mixture (i.e., about 0.01 to about 20 parts by weight, based on 100 parts by weight of the monomer material).

The reaction mixture also comprises a solvent. Suitable solvents include any in which the monomer and internal crosslinking agent are substantially soluble and in which the superabsorbent polymer and blowing agent are substantially insoluble. Suitable solvents will also have a vaporization temperature which is greater than the vaporization temperature of the blowing agent and the critical temperature of the reaction mixture, and preferably greater than the activation temperature. In the preferred embodiment where substantially water-soluble monomers are used, the solvent is preferably water, a water-soluble alcohol (e.g., lower alcohols such as methanol, ethanol, propanols, and butanols), or mixtures of any two or more of such compounds. Most preferably, the solvent is water. Although the concentrations of the various components of the reactant mixture may be widely varied as long as the dispersion, stabilization, expansion, and reaction steps can be effected, the reaction mixture will generally comprise about 1 part by weight of the monomer to about 1 part by weight of solvent.

The reaction mixture may also contain various optional components, including surfactants, polymerization initiators, and viscosity control agents. Conventional additives for absorbent gelling materials, such as antioxidants and deodorants, may also be included.

It is particularly desirable to include at least one surfactant in the reaction mixture. The surfactant may be any of those generally known in the foam art, selected for its ability to stabilize the dispersion of the blowing agent in the reaction mixture. The surfactant may aid in the formation of a superabsorbent polymer foam having a desired morphology. The surfactant is believed to be particularly useful for obtaining relatively small average cell sizes and relatively narrow cell size distributions by influencing the particle size and particle size distribution of the blowing agent.

Where the solvent is water or water-soluble and the blowing agent is substantially water-insoluble, suitable surfactants include nonionic surfactants possessing both hydrophilic and hydrophobic groups. One or more surfactants to provide such groups may be used. The presence of both hydrophilic groups and hydrophobic groups may serve to enhance stabilization by preventing phase separation into an "oily" blowing agent phase and a "water" reactant phase. A mixture of such groups allows for tailoring of the surfactant system to enhance stabilization of the dispersion, depending on the respective hydrophilicity or hydrophobicity of the components of the reaction mixture. In general, as the ratio of hydrophobic groups to hydrophilic groups in the surfactant increases, stabilization is further enhanced, provided that sufficient hydrophilic groups to prevent phase separation are present. Preferably, the surfactant (or surfactant mixture) is selected to match the hydrophile-lipophile balance (i.e., HLB) value of the blowing agent. For substantially water-insoluble blowing agents, the blowing agent is more readily stabilized as the HLB value of the surfactant decreases. A system of matching the HLB value of an emulsifier to one or more ingredients to be emulsified is described in the technical bulletin *Meaning of HLB Advantages and Limitations*, ICI Americas Inc., 1984, incorporated herein by reference.

The nonionic surfactant is preferably selected from the group consisting of linear alkoxylated alcohols, linear alkylphenoxylated alcohols, and esters thereof. Preferred are the ethoxylated copolymers of sorbitan fatty acid esters such as the ethoxylated copolymers of sorbitan monolaurate (available as TWEEN ®20, ICI Americas, Inc.) and of sorbitan monooleate (available as TWEEN ®80, ICI Americas, Inc.). Mixtures of the forementioned surfactants with substantially hydrophobic (i.e., lipophilic) surfactants, may also be used. Suitable hydrophobic surfactants include sorbitan fatty acid esters such as sorbitan monolaurate (available as SPAN ®20, ICI Americas, Inc.) and sorbitan monooleate (available as SPAN ®80, ICI Americas, Inc.).

While the amount of surfactant may be varied, it is generally desirable to use the minimum level needed to effect stabilization of the blowing agent. Use of the minimum level may prevent or minimize an adverse impact on the absorptive properties of the resultant foam due to residual surfactant and generally provides a product cost benefit. The surfactant will typically be used in an amount of about one-tenth the amount of the blowing agent. The surfactant can be added to the reaction mixture or pre-mixed with the blowing agent which is later dispersed in the reaction mixture.

The optional initiator is particularly useful to initiate polymerization, generally of the monomer and the internal crosslinking agent. An initiator is usually preferred since it typically lowers the activation temperature of the internal crosslinking agent. An initiator is particularly suitable where an increased rate of reaction is desired, and is therefore generally preferred for cost-effective manufacturing. In addition, an initiator is particularly useful where the foam is formed on a wicking substrate. Upon activating the initiator and thereby initiating polymerization, the viscosity of the dispersion typically increases. The increase in viscosity may serve to facilitate the formation of a desired foam pattern on the wicking substrate.

The initiator may be any conventional polymerization initiator. The initiator is preferably substantially soluble in the solvent and is selected based, in part, on the intended method of inducing the reaction of the monomer. Thus, light and heat activated initiators are useful initiators. For example, where thin films of the foams are desired, a light activated initiator may be used to effect rapid reaction when the mixture is exposed to a light radiation source. The optional polymerization initiators include free radical initiators including, for example, per oxygen compounds such as sodium, potassium, and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate, and the like. Conventional redox initiator systems can also be used, e.g., systems combining the foregoing peroxygen compounds with reducing agents such as sodium bisulfite, L-ascorbic acid or ferrous salts. The amount of the initiator used may be that amount conventionally used in the polymer field. Typically, the initiator is used at a level of up to about 5 mole percent, preferably about 0.001 to 0.5 mole percent, based on the total moles of polymerizable monomer.

Another preferred, optional component of the reaction mixture is a viscosity control agent. The viscosity control agent generally serves to increase the viscosity of the reaction mixture and is particularly useful for controlling the particle size of the blowing agent which is dispersed in the reaction mixture. In general, as the viscosity of the reaction mixture increases the particle size is more readily controlled. Thus, the viscosity control agent may be used to disperse and stabilize the blowing agent in the reaction mixture. The viscosity control agent may also facilitate coating or printing of the stable dispersion onto a substrate, particularly a wicking substrate. By increasing the viscosity of the reaction mixture, the agent may facilitate the formation of a desired foam pattern on the substrate. The viscosity control agent may also prevent or minimize separation of the solvent from the reaction mixture (i.e., partitioning), particularly when the stable dispersion is applied to a wicking substrate, thereby promoting the formation of a uniform product having optimum properties. Suitable viscosity control agents are preferably substantially soluble in the solvent. Exemplary water-soluble viscosity control agents are carboxymethyl cellulose, hydroxyethyl cellulose, and polyacrylic acid. The viscosity control agent is typically added in an amount of less than about 2%, more typically less than about 1%, by weight of the total monomer.

Formation of a Stable Dispersion

A stable dispersion of a blowing agent is formed in the reaction mixture by adding a blowing agent to the reaction mixture, typically either during or after formation of the reaction mixture; dispersing the blowing agent; and stabilizing the dispersion. The blowing agent is dispersed in the reaction mixture and stabilized so as to form a stable discontinuous phase of the blowing agent (i.e., "particles" of blowing agent) in the reaction mixture phase. The blowing agent particles are relatively free of the monomer, internal crosslinking agent, and solvent.

Suitable blowing agents include any conventional blowing agent which is substantially insoluble in the solvent and whose particle size can be controlled and stabilized when dispersed in the reaction mixture. In addition, the blowing agent will be capable of controlled expansion. Suitable blowing agents also have a vaporization temperature (i.e., boiling point) which is less than the vaporization temperature of the solvent, at a given pressure. The blowing agent will preferably also have a boiling point which is less than the critical temperature, so as to allow sufficient expansion of the blowing agent before the formation of the substantially water-insoluble polymer. Exemplary blowing agents are disclosed in *Chemical Encyclopedia*, H. Lasman, National Polychemicals, Inc., Vol. 2 at page 534, incorporated herein by reference. In the preferred embodiment in which water is used as the solvent, suitable blowing agents are substantially water-insoluble liquids having a boiling point of less than about 100° C., more preferably less than about 80° C., most preferably less than about 50° C. Typically, the blowing agent will have a boiling point in the range of about −20° C. to about 80° C., preferably about −20° C. to about 50° C. Such blowing agents include aliphatic and aromatic hydrocarbons and halohydrocarbons, which may be cyclic or alicyclic, linear or branched, and saturated or unsaturated. Exemplary blowing agents include the pentanes, hexanes, heptanes, benzene, substituted benzenes, chloromethanes, chloroethanes, chlorofluoromethanes, and chlorofluoroethanes such as described in the above referenced *Chemical Encyclopedia*. Preferably a pentane (e.g., n-pentane, 2-methylbutane, and/or 2,2-dimethylpropane) or 1,1,2-trichlorotrifluoroethane is used. While the amount of blowing agent employed can vary over a wide range consistent with obtaining a foam having a desired morphology, the blowing agent will generally be added at a level of about 5 to about 50 parts per 100 parts (by weight) of monomer. Typically, about 20 to about 30 parts of blowing agent per 100 parts (by weight) of monomer are used.

The blowing agent may be dispersed by applying shear stress (e.g., through high shear mixing) to the reaction mixture and, if necessary, by controlling the viscosity ratio of the blowing agent phase to the reaction mixture phase (as used herein, the viscosity ratio refers to the viscosity of the blowing agent phase divided by the viscosity of the reaction mixture phase) and/or by using a surfactant. The dispersion process is controlled so as to obtain a desired blowing agent particle size. The particle size of the dispersed blowing agent influences the cell size (including cell size distribution), the intercommunication of foam channels, and the surface area to mass ratio of the resultant superabsorbent polymer foam. Particle size influencing features include the shear rate, surfactant type, the viscosity ratio, and the isotropy of the reaction mixture. Preferably, these features are controlled so as to minimize the blowing agent particle size. The blowing agent is typically dispersed to a particle size of less than about 10 microns, preferably less than about 5 microns, more preferably less than about 2 microns. The minimum particle size is typically about 0.1 microns.

For obtaining a relatively small blowing agent particle size, it is preferred to use a relatively high shear stress for dispersing the blowing agent. In general, the higher the rate of shear, the smaller the average particle size of the blowing agent. Where particles of substantially uniform size are desired, it is typically preferred to have uniform shear throughout the mixture.

For a given reaction mixture, blowing agent, temperature, and shear stress, the particle size of the blowing agent typically decreases as the viscosity ratio of the dispersed blowing agent phase to the continuous reaction mixture phase is decreased. As the viscosity ratio decreases, the blowing agent particle size is more readily controlled to a smaller particle size. Therefore, it is generally preferred to minimize the viscosity ratio. Typically, the dispersion is such that the viscosity ratio is less than about 0.5, more preferably less than about 0.25.

The viscosity ratio is preferably decreased by using a viscosity control agent in the continuous reaction mixture phase and/or a low viscosity blowing agent. The viscosity ratio may also be varied by varying the reaction conditions, for example, the temperature or reactant concentration of the reaction mixture ("reactant" refers to the superabsorbent-polymer-forming materials, including the monomer and internal crosslinking agent). In general, as the temperature decreases or the reactant concentration increases, the viscosity ratio will decrease. The viscosity ratio will also vary with the reactivity of the specific superabsorbent-polymer-forming materials that are present in the reaction mixture. The reaction conditions and reactant types may be varied to control the rate of reaction in solution and therefore the solution viscosity. In general, as the reaction progresses toward formation of the substantially water-insoluble polymer material (e.g., as a linear polymer of the monomer is formed), the solution viscosity will increase and the viscosity ratio will decrease. In addition, the viscosity ratio may be decreased by initially using a substantially water-soluble polymer of the monomer as a superabsorbent-polymer-forming material in the reaction mixture. Where a relatively uniform particle size is desired, it is preferred that the reaction mixture be substantially isotropic, i.e., the components of the reaction mixture are blended such that they are substantially uniform throughout the mixture.

The dispersion having the desired blowing agent particle size is preferably stabilized prior to the expansion and reaction steps to form the substantially water-insoluble polymer foam. Preferably, stabilization occurs simultaneously with dispersion. By "stable", "stabilized", etc., it is meant that the desired particle size of the dispersed blowing agent is maintained for a time sufficient to allow reaction of the monomer and internal crosslinking agent to form the substantially water-insoluble polymer foam having a desired morphology, e.g., substantially continuous intercommunicating channels substantially throughout the foam and a relatively small cell size, low density, and high surface area to mass ratio.

Any method of stabilizing the dispersion may be employed. Preferably, a surfactant is used to stabilize the dispersion. In general, the smaller and more uniform the blowing agent particles, the more stable the dispersion. Therefore, stabilization may also be aided by controlling the viscosity ratio. In general, the lower the viscosity ratio at a given shear, the smaller the particle size of the blowing agent and the more stable the dispersion.

Expansion and Reaction

After forming the stable dispersion of the blowing agent having the desired particle size, the blowing agent is expanded to form an expanded structure, and the monomer or the monomer and the internal crosslinking agent are reacted to form a substantially solvent-insoluble polymer (i.e., an expanded, substantially solvent-insoluble polymer structure is formed). In the preferred embodiment where the solvent is water, the polymer is substantially water-insoluble.

The expansion and reaction are controlled such that, by the time the substantially water-insoluble polymer is formed, the expanded structure has a morphology substantially as desired in the superabsorbent polymer foam ( the polymer need not be superabsorbent by :the point of insolubility). Preferably, the expansion of the blowing agent is controlled along with the reaction of the monomer or the monomer and the internal crosslinking agent so as to provide a superabsorbent polymer foam having substantially continuous intercommunicating channels substantially throughout the foam, an average cell size of less than about 100 microns, a surface area to mass ratio of at least about 0.2 $m^2/g$, and a density of less than about 0.5 $g/cm^3$.

In general, the blowing agent particles of the stabilized dispersion are expanded so as to avoid excessive coalescence of the blowing agent as it expands, i.e., the blowing agent particles generally expand in relative proportion to their initial stabilized particle size and shape in the dispersion. Typically, the blowing agent particles are expanded to about 10 times their original size. During or after expansion (preferably after), the monomer and or monomer and internal crosslinking agent are reacted to form the substantially water-insoluble polymer so as to stabilize the expanded structure (a substantially water-insoluble polymer foam is formed).

In general, the rate of expansion of the blowing agent and the viscoelastic properties of the reaction mixture as the substantially water-insoluble polymer forms are controlled simultaneously so as to provide an open-celled foam having a desired morphology. If expansion is too rapid or too slow relative to the formation of the substantially water-insoluble polymer, the foam may not have a desired morphology, particularly a desired surface area to mass ratio. The elasticity of the reaction mixture and/or forming polymer should be capable of supporting the formation of the substantially water-insoluble polymer material generally in a size and shape proportional to the expanded blowing agent particles. In general, the elasticity of the reaction mixture and/or forming polymer should be capable of withstanding the vapor pressure of the expanding blowing agent.

For any given reaction mixture, there is a critical viscosity at which a foam having a desired morphology is difficult to achieve. The critical viscosity corresponds to a critical temperature, described below. The critical viscosity is typically reached when the monomer or monomer and internal crosslinking agent have polymerized such that the visco-elastic properties of the resultant polymer make it difficult to form an open-celled foam. Therefore, in preparing the foams herein, the blowing agent particles are preferably expanded to form an expanded structure before the critical viscosity of the reaction mixture is reached. More preferably, the expanded structure has substantially the finally desired superabsorbent polymer foam morphology by the time the critical viscosity is reached. Preferably, at least about 90%, more preferably at least about 95%, of the ultimately desired open cells are formed before the point of critical viscosity.

At the point of critical viscosity, the polymer is typically substantially water-insoluble. The substantially water-insoluble polymer may be formed by polymerization of the monomer alone. This reaction can be initiated by heat and/or light radiation. The resultant polymer may be further reacted to form a superabsorbent polymer material, e.g., by reacting the polymer with a crosslinking agent (and neutralizing carboxyl groups of the polymer as may be necessary). In the preferred embodiment where an internal crosslinking agent is present in the reaction mixture, the polymer is crosslinked by heating the expanded, substantially water-insoluble polymer structure to a temperature greater than the critical temperature, generally to at least the activation temperature. Alternatively or in addition to the internal crosslinking agent, the polymer structure may be reacted with an external crosslinking agent.

The substantially water-insoluble polymer may also be formed by reaction of the monomer (or a substantially water-soluble polymer thereof) and the internal crosslinking agent. This reaction is typically initiated by heat, either directly applied to the reactants or as generated by a monomer polymerization reaction induced by light radiation. The resultant polymer may be further reacted as may be necessary to form a superabsorbent polymer material, e.g., by subjecting the expanded polymer structure to higher temperatures or by reacting the polymer of the structure with additional crosslinking agent (and neutralizing carboxyl groups of the polymer as may be necessary).

Where the reaction to form a substantially water-insoluble polymer is initiated by heat, there is a critical temperature at which the reaction typically occurs. The critical temperature corresponds to the critical viscosity and thus typically to the formation of a substantially water-insoluble polymer. The critical temperature and critical viscosity will vary with the particular reaction mixture composition, e.g., the menomer, internal cross-linking agent, and the optional initiator.

The critical temperature may be determined for a given reaction mixture by determining the maximum rate of change in the viscosity of the reaction mixture as a function of temperature. The viscosity of the reaction mixture at various temperatures can be determined by known rheometry methods. As used herein, viscosity refers to the apparent viscosity, i.e., viscosity is meant to characterize the full spectrum of fluids or dispersions. This full spectrum includes simple Newtonian fluids for which viscosity is the proportionality constant that relates shear force per unit area to the negative of the local velocity gradient, and other fluids that are not typically included by this simple law (e.g., pastes, slurries, high molecular weight polymers and dispersions of insoluble materials mixed with soluble materials). These concepts are described in greater detail in *Transport Phenomenon*, Bird, et al., John Wiley & Sons, Inc. (1966), Chpt. 1, incorporated herein by reference.

Since the critical temperature may vary with the reaction rate of a given reaction mixture and therefore the time for which the reaction mixture is maintained at a given temperature, the viscosities are measured for a reaction mixture which has been maintained at various temperatures for a constant time period at each temperature. This is most readily done by using a rheometer capable of heating a reaction mixture sample at a controlled rate. Suitable rheometers include a Sangamo Visco-Elastic Analyzer and a Brabender blender and rheometer. The principle of operation of a blender and rheometer such as the Brabender system is described in the *Handbook of Polymer Science and Technology. Vol. 3: Applications and Processing Operation*, Cheremisinoff, Marcel Dekker Inc. (1989), pages 373–419. Alternatively, the viscosity of separate samples of a given reaction mixture may be determined with the viscosity of the individual samples being measured after being held for a constant time period at a given temperature for a given sample.

Figure 5:
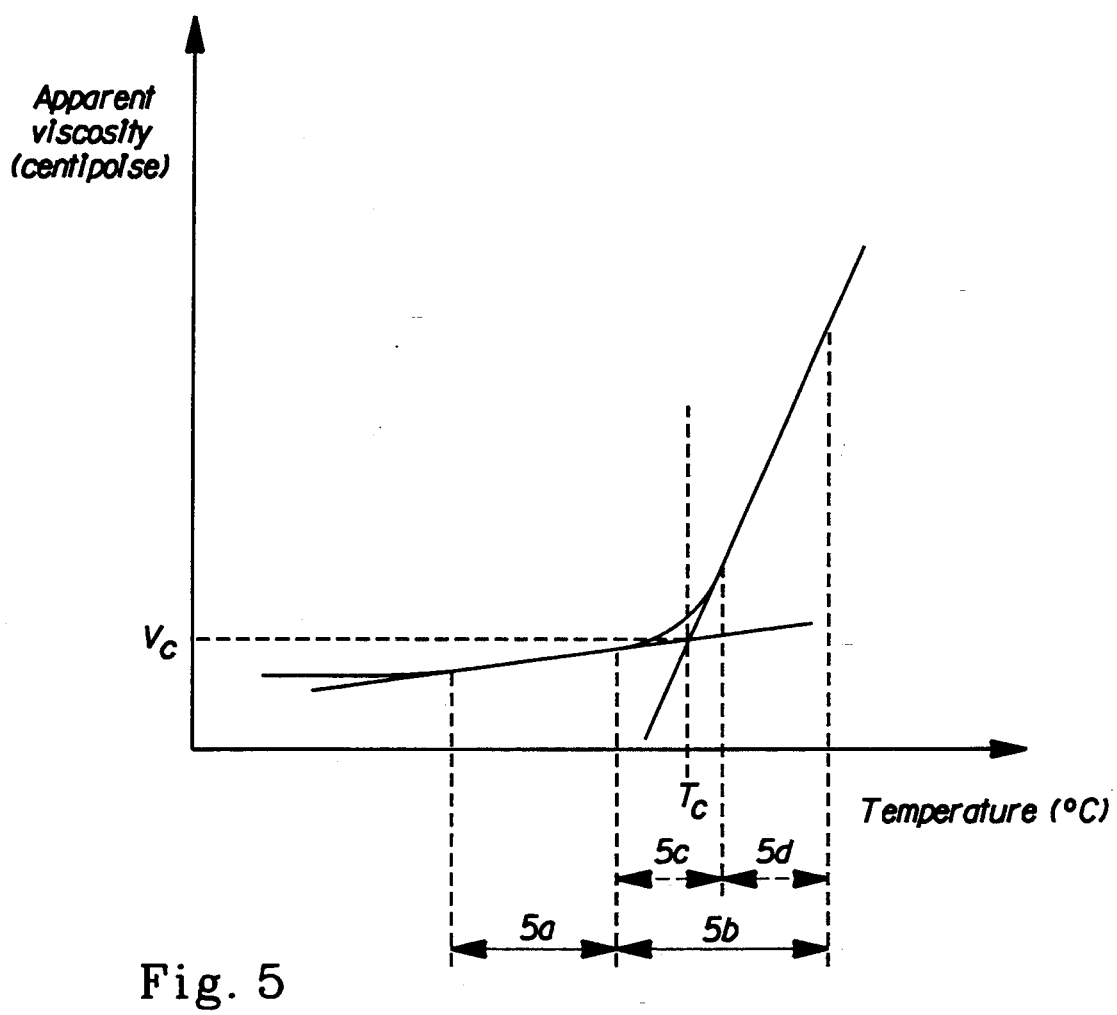
FIG. 5 is a graph showing a relationship of viscosity and temperature for a reaction mixture of the present invention.

The viscosity is plotted as a function of temperature, the resultant curve typically being as shown in FIG. 5. As shown in FIG. 5, the resultant curve has an initial, substantially linear, slightly sloping part 5a corresponding to a small change in viscosity per unit change in temperature, and a second part 5b of rapidly increasing slope corresponding to a rapid increase in viscosity per unit change in temperature. At least the first part 5c of this second part 5b may be described as a parabolic, corresponding to an exponential increase in viscosity per unit change in temperature. This paraboloid part 5c is followed by a substantially linear, steeply sloping part 5d.

As shown in FIG. 5, the critical temperature ($T_c$) and critical viscosity ($V_c$) are determined from the point of intersection of the line tangent to the substantially linear, slightly sloping part 5a and the line tangent to the substantially linear, steeply sloping part 5d. The critical temperature and critical viscosity are determined by extrapolating from the point of intersection to the x-axis ($T_c$) and the y-axis ($V_c$).

In some cases the parabolic part 5c may not be followed by a substantially linear part but the curve may, for example, remain parabolic. In addition, for some systems it may be difficult to measure the viscosity for all points on the parabolic curve (i.e., above a certain temperature). In such cases the critical temperature may be determined through calculus methods. The first derivative of the curve (viscosity as a function of temperature) is determined for various temperatures and is plotted as a function of those temperatures. The resultant curve is typically characterized by a maximum inflection point which corresponds to the maximum rate of change in the viscosity of the reaction mixture as a function of temperature. The temperature which corresponds to this maximum rate of change can be determined graphically and is the critical temperature.

In order to carry out the expansion step before the critical viscosity is reached, the blowing agent particles of the stable dispersion will typically be expanded by heating the stable dispersion to a temperature which is greater than or equal to the vaporization temperature of the blowing agent and less than or equal to the critical temperature, preferably less than the critical temperature, most preferably about 5° C. to about 10° C. less than the critical temperature. Therefore, the blowing agent is preferably selected such that it will volatilize (vaporize) at such a temperature. In an alternative embodiment of the present invention, the expansion is caused by decreasing the pressure on the stable dispersion. In addition, various combinations of pressures and temperatures may be selected in order to expand the dispersion.

Where a decrease in pressure alone is used to expand the blowing agent, the critical viscosity is not generally attained in the expansion step. In such case, it is important to form the substantially water-insoluble polymer at about the point where the expanded structure has substantially the same morphology as that desired in the final foam. This will typically be achieved by increasing the temperature of the expanded structure to at least the critical temperature to cause reaction of the monomer or the monomer and internal crosslinking agent to form the substantially water-insoluble polymer.

It is generally preferred to expand the blowing agent as slowly as possible. Typically, the blowing agent is expanded by heating the stable dispersion to the vaporization temperature of the blowing agent at a rate of less than about 1° C./minute, more preferably less than about 0.5° C./minute, most preferably less than about 0.1 to about 0.2° C./minute. The rate of heating may be increased if a counterpressure is applied to the dispersion in order to achieve substantially the same rate of expansion as where only the temperature is increased at the preferred rates. Alternatively, where a decrease in pressure is used to expand the blowing agent, a corresponding (at a given temperature) controlled rate of decreasing pressure may be used to form the expanded structure.

As previously stated, the monomer or the monomer and internal crosslinking agent of the expanded structure are reacted so as to form an expanded structure comprising a substantially water-insoluble polymer (i.e., a substantially water-insoluble foam is formed). Reaction can be caused by heating the expanded structure to at least the critical temperature. Preferably the expanded structure is heated to the critical temperature.

The monomer and internal crosslinking agent are then reacted to form a network crosslinked, typically superabsorbent, polymer. Such reaction is caused by heating the structure to at least the activation temperature. The activation temperature may be equal to or greater than the critical temperature. Preferably, the reaction mixture is designed (more particularly, the internal crosslinking agent and/or initiator is selected) such that the activation temperature is greater than the critical temperature, more preferably at least about 10° C. to about 20° C. above the critical temperature. Network crosslinking is described in greater detail below.

The rate of heating to cause reaction of the monomer (or polymer thereof) and the internal crosslinking agent to form the network crosslinked polymer is preferably slow in order to avoid the rapid volatilization of any residual blowing agent and to prevent or minimize disruption of the expanded structure. Where the activation temperature is greater than the critical temperature, the rate of heating to cause reaction need not be as slow as the rate of heating to cause expansion. Preferably, the rate of heating to cause reaction is less than about 10° C./minute, more preferably from about 5° C. about 10° C./minute, most preferably from about 8° C. to about 10° C./minute.

Although the various components of the stable dispersion may be selected such that the blowing agent vaporization temperature, the critical temperature, and the activation temperature are the same, for the preferred foams herein, those components are selected such that the blowing agent vaporization temperature is less than the critical temperature which itself is less than the activation temperature. Most preferably the components are such that the blowing agent vaporization temperature is from about 5° C. to about 10° C. less than the critical temperature which itself is from about 10° C. to about 20° C. less than the activation temperature.

The expansion and reaction conditions are preferably uniform throughout the dispersion and/or the expanded structure. Uniformity is generally achieved by ensuring a relatively isotropic reaction mixture and a uniform temperature and/or pressure throughout the dispersion and/or the expanded structure. Uniformity of temperature and pressure are influenced by the heating means, the volume and/or depth of the dispersion being reacted, the heat flux (i.e., rate of heating), and the extent of exothermic heat evolution by the reacting dispersion. Preferably, these factors are Controlled so as to ensure uniform heat transfer (i.e., temperature gradients across the expanding material are minimized) throughout the dispersion and/or the expanded structure. For forming a bulk foam material, a particularly suitable reactor for ensuring uniform heat transfer is a stirred tube reactor. In forming thin films (e.g., having a thickness of from about 1 mil to about 500 mils) of the foam, it will generally be suitable to use ultraviolet, infrared, microwave and/or electron beam radiation to cause expansion and/or reaction. For achieving a rapid rate of reaction in such thin films, it is generally preferred to use ultraviolet radiation. However, as the thickness of the foam to be formed increases over about 500 mils, it is preferred to use infrared and/or electron beam radiation in order to prevent or minimize nonuniform cell structure.

The expansion and/or reaction step can occur in a closed or open environment. For example, expansion can take place in a closed mold. The expansion and/or reaction step may also occur in an open system, such as on a web upon which the stable dispersion has been applied, for example, by extrusion or printing. The dispersion may be applied to a temporary or permanent substrate prior to its expansion and reaction to form the polymer foam.

As previously stated, the substantially water-insoluble polymer is reacted to form a substantially water-insoluble, network crosslinked polymer. The reaction is typically caused by heating the expanded substantially water-insoluble polymer structure to the activation temperature. As noted above, the activation temperature may be equal to the critical temperature, in which case crosslinking coincides with insoluble polymer formation. In such case, no additional reaction is generally required (although further crosslinking may be used to modify absorptive properties).

Conditions for reacting the substantially water-insoluble polymer to form a network crosslinked polymer may be selected consistent with the above teachings from polymerization conditions such as are generally described in the above referenced U.S. Pat. No. Re. 32,649 and in U.S. Pat. No. 4,666,983 issued to Tsubakimoto et al.; and U.S. Pat. No. 4,62S,001 issued to Tsubakimoto et al.. Such reaction conditions generally involve heating (i.e., thermal activation techniques) the polymer to a temperature of from about 0° C. to about 100° C., more preferably from about 20° C. to about 80° C., most preferably from about 50° C. to about 80° C. Temperatures of less than about 80° C. are preferred for obtaining foams having a low extractable polymer content. Conditions under which the polymer is maintained can also include, for example, subjecting the polymer to any conventional form of polymerization activating radiation. Radioactive, electronic, ultraviolet, or electromagnetic radiation are suitable alternative conventional polymerization techniques.

"Network" crosslinking refers to the reaction of reactive sites of the monomer or polymer thereof with the reactive sites of the internal crosslinking agent to form a three-dimensional polymer network in which there are crosslink bonds between different polymer chains, the polymer chains being generally attributable to polymerization of the monomer. Sufficient network crosslinking provides a substantially water-insoluble polymer. Sufficient network crosslinking, which may or may not be the same degree as required to provide substantial insolubility, also renders the polymer superabsorbent (where a sufficient number of neutralized carboxyl groups are present in the polymer). Thus, additional crosslinking of the insoluble polymer material may be required in order to render it superabsorbent. The level of crosslinking of the insoluble polymer material is generally determined by the reactant type (particularly the crosslinking agent) and concentration and the reaction conditions. Therefore, if necessary, the substantially water-insoluble polymer material can be made superabsorbent by exposing it to more extreme reaction conditions and/or additional crosslinking agent. (Since superabsorbency is also influenced by the level of salt groups in the polymer, various degrees of superabsorbency may also be imparted by neutralizing at least a portion of the salt-forming groups (e.g., carboxyl groups) of the polymer as previously described.)

The degree of network crosslinking, i.e., the crosslink density, may be varied as known in the art to provide various gel strengths and gel volumes as may be desired. In general, as the crosslink density increases, the gel strength increases, gel volume decreases and, at a constant surface area to mass ratio, the rate of absorption decreases. Thus, the degree of network crosslinking in part serves to determine the absorptive capacity and absorptive rate of the superabsorbent polymer material and thus of the superabsorbent polymer foam. The degree of network crosslinking also influences the residual monomer and extractable polymer content of the foam. In a preferred embodiment, the internal crosslinking agent and monomer are reacted so as to form a substantially water-insoluble superabsorbent polymer material which is partially network crosslinked so as to achieve a desired gel strength and gel volume.

In the preferred embodiment in which the solvent is water and the expansion and reaction has occurred at temperatures less than the boiling point of water ( i.e., 100° C. at 1 atm), the resultant foam will typically comprise water as absorbed from the reaction mixture by the superabsorbent polymer material of the foam. Some level of water is generally desired in the foams in order to enhance the flexibility and absorptive rate of the foam. S Preferably, the foam will contain less than about 20%, more preferably less than about 10%, most preferably less than about 5% by weight of water per 100 parts by weight of the superabsorbent polymer material of the foam. (These preferred percentages include any water which may be absorbed from the environment.) The level of water may be controlled by varying the amount of water used in the reaction mixture. In addition, water may be added to the superabsorbent polymer foam (e.g., as an external plasticizer). Although it will usually be unnecessary, the water content may be decreased by, for example, displacing the water with a lower alcohol such as those described herein and/or by heating the foam to evaporate the water, e.g., by microwave radiation.

Where the solvent is other than water, any remaining solvent may be removed in whole or part from the resultant foam. This is most readily carried out by heating the foam material to a temperature sufficient to evaporate the solvent within a reasonable time, e.g., near or above the boiling point of the solvent.

Typically, the components of the reaction mixture and the blowing agent are introduced into a vessel equipped for high shear mixing, and the stable dispersion as described above is formed in the vessel. The blowing agent is then expanded and the monomer and internal crosslinking agent are reacted to form the foam. The foam is typically shaped during and/or after its formation. Shaping may be achieved by any conventional shaping techniques as are known in the art to form a foam having a defined shape and size. Preferred methods for shaping the foam include casting, molding, or forming operations.

Casting and molding techniques generally involve introducing the stable dispersion into a prepared mold cavity (open or closed mold) and causing expansion and reaction such that the foam conforms to the shape of the mold cavity. Examples of specific molding techniques for use herein include compression molding, injection molding, extrusion, or laminating. Forming techniques involve performing various operations on the stable dispersion or foam to modify its shape and/or size. Examples of specific forming techniques for use herein include grinding, chopping, cutting, coating and extruding operations. For example, the stable dispersion may be extruded through an orifice to form a foam having a shape corresponding to the shape of the orifice. Further, the stable dispersion may be cast on a surface to form a foam having a desired shape or surface morphology. Any or all of these techniques may also be used in combination to form the shaped foam. Any suitable apparatus as are known in the art may be used to carry out such operations.

The superabsorbent polymer foams of the present invention are useful in free form, including particulate (includes granules, chunks, and the like), sheet or other three-dimensional forms. A particulate foam material can be obtained from a bulk sample of foam material by any suitable method, e.g., chopping or grinding. However, in any such process it will generally be desired to make efforts to substantially preserve the morphology (e.g., surface area to mass ratio) of the foam material as originally formed. To form a free (i.e., unsupported) foam sheet, the stable dispersion is applied to a temporary substrate followed by expansion of the blowing agent and reaction of the internal crosslinking agent with the monomer to obtain the substantially water-insoluble, polymer foam. The foam is then readily removed from the temporary substrate. Temporary substrates include any materials known for such purpose, e.g., TEFLON ® sheets, MYLAR ® sheets, and release-coated metal sheets. The stable dispersion may be applied to the substrate by any conventional method of preparing films or prints, for example, knife-coating, spray-coating, reverse-roll coating, gravure-coating, cold extrusion coating or casting, and the like. The stable dispersion may be applied to the substrate to obtain a foam product in a desired shape. Alternatively, the foam product may be cut to a desired form.

The superabsorbent polymer foams of the present invention are also useful when joined to a carrier to form an absorbent member. The carriers may be any carriers as are known in the art such as nonwoven webs, tissue webs, conventional foams, polyacrylate fibers, apertured polymeric webs, synthetic fibers, metallic foils, elastomers, and the like. The carrier may be any material generally employed for use in absorbent articles, including wicking and non-wicking materials. Examples of wicking carriers include tissue paper (which includes paper toweling). Examples of non-wicking carriers include polymer films such as polypropylene. For use in absorbent articles, a particularly suitable carrier is paper tissue. For example, suitable paper tissue is disclosed in U.S. Pat. No. 4,191,609 issued to Trokhan on Mar. 4, 1980; U.S. Pat. No. 4,529,480 issued to Trokhan on Jul. 16, 1985; and U.S. Pat. No. 4,637,859 issued to Trokhan on Jan. 20, 1987, each incorporated herein by reference. Suitable carriers also include any of the backsheet materials described herein for use in absorbent articles. The carrier may be of any desired shape and may be shaped before, during or after joinder with the foam.

The foam may be joined to the carrier via chemical or physical bonding methods such as are known Including adhesives or chemicals that react to adhere the foam to the carriers. Joinder is also meant to include generally non-bonded combinations of the foam with other materials, e.g., encasing or sandwiching the foam in or between other materials. Alternatively, the foam can be joined to the carrier by applying the stable dispersion to the carrier and causing expansion and reaction so as to form the foam on the carrier (i.e., the carrier is a permanent substrate) to provide a superabsorbent foam-bearing structure. The foams as joined to the carrier by any one of these methods can be in a continuous or discontinuous form or pattern.

Where the foam is formed on the carrier (i.e., the carrier is a permanent substrate), the carrier and foam material are preferably selected such that there is sufficient bonding (physical and/or chemical) of the foam to the carrier as required by the intended application. The stable dispersion can be applied to the entire surface of the carrier or to any portion thereof and in any continuous or discontinuous pattern. Suitable patterns can be selected for tailoring the absorption properties of the foam-bearing structure as may be desired. For example, for use in disposable diapers, particular patterns may be formed to provide defined absorption properties in diapers for female or male use.

In a preferred embodiment of the present invention, the stable dispersion is transferred to and extruded through a conventional extruder apparatus. An example of an extruder apparatus is shown in FIGS. 12-14 of *Principles of Polymer Materials, Second Edition* (McGraw-Hill Book Co., 1982) at page 331, which is incorporated herein by reference. The stable dispersion is extruded through the orifice of the extruder apparatus onto a temporary or permanent web substrate, followed by the expansion and .reaction steps to form a free foam sheet or a foam-bearing structure. The temperature and pressure can be controlled in the extruder so as to control the expansion and reaction process. For example, polymerization of the monomer to form a substantially linear polymer may be caused while the mixture is in the extruder. Expansion and reaction of the linear polymer, any remaining monomer, and the internal crosslinking agent to form a substantially water-insoluble foam may then be caused when the dispersion is at or beyond the orifice.

In another preferred embodiment, the stable dispersion is printed onto a permanent substrate followed by expansion and reaction to form a foam-bearing substrate. Exemplary printing apparatus and techniques include rotogravure and flexographic printing equipment and processes such as disclosed in *Flexography Principles and Practices, 4th Edition,* Flexographic Technical Association, Inc., 1991, incorporated herein by reference. The permanent substrate may be any of those discussed herein, preferably a wicking material, more preferably comprising cellulosic fibers, most preferably wood pulp fibers.

Where a wicking substrate is used, it is particularly desirable to print the stable dispersion in a discontinuous pattern on the wicking substrate in order to form an absorbent member possessing both the capillary absorptive properties of the wicking material and the osmotic absorptive properties of the resultant discontinuous pattern of superabsorbent foam. To form the discontinuous pattern, it is generally desirable to use a stable dispersion having a sufficiently high viscosity such that wicking of the dispersion into the substrate does not occur to a substantial extent. In this way, the wicking properties of the substrate are substantially maintained in addition, the higher viscosity may prevent or minimize partitioning of the solvent and the reactants. The viscosity can be controlled by any of the methods discussed herein in reference to forming the stable dispersion, e.g., through the use of a viscosity control agent and/or multi-step reaction process. In addition, it is generally desirable to initiate expansion and reaction to form the foam within a short time, preferably immediately, after printing of the stable dispersion onto the substrate. For example, polymerization of the monomer to form a linear polymer may be initiated by, e.g., subjecting the printed dispersion to ultraviolet radiation. Expansion and reaction of the linear monomer, any remaining monomer, and the internal crosslinking agent in the printed dispersion is then caused, e.g., by subjecting the printed dispersion to heat. The ultraviolet radiation used to initiate polymerization of the monomer may be sufficient where the blowing agent has a sufficiently low boiling point and the crosslinking agent has a sufficiently low activation temperature. If necessary, additional sources of heat may be used, e.g., infrared radiation.

In an especially preferred embodiment, the superabsorbent polymer foam of the present invention is flexibilized. Flexibilization may be achieved by including suitable "internal" plasticizers in the reaction mixture, the plasticizers being reactive with at least one of the superabsorbent-polymer-forming materials. Certain internal plasticizers may be used as a monomer component of the reaction mixture, either solely or in admixture with other monomers described above, provided that they meet the description of those monomers. Such monomers can be selected by one having ordinary skill in the art in view of this disclosure.

The internal plasticizers include unsaturated materials capable of reacting under the above-described polymerization conditions to form an addition-type polymer material, or the addition polymer itself. The addition polymers will have a relatively low glass transition temperature (i.e., Tg), e.g., less than about 25° C. The plasticizer may possess hydrophilic groups such as acid or other functional groups. Suitable internal plasticizers include olefins, aromatic ethylenically unsaturated monomers, and C1–C24 alkyl esters of unsaturated carboxylic acids. Preferably, the internal plasticizer is isobutylene or 2-ethyl hexylacrylate.

The type and level of internal plasticizer can be selected by one having ordinary skill in the art in order to obtain a superabsorbent polymer foam having various degrees of flexibility. Preferably, the foam is designed such that an absorbent article such as a diaper or feminine hygiene product is sufficiently compliant so as to readily conform to the general shape and contours of the wearer's body.

In place of or in addition to the internal plasticizer, an "external" plasticizing compound may be used to provide flexibility in the resultant superabsorbent polymer foam. External plasticizers generally include plasticizing compounds other than the above addition polymers and addition-polymer-forming materials. Such plasticizers include hydrophilic compounds and hygroscopic compounds. Exemplary hydrophilic compounds are water and relatively higher molecular weight polyols such as polyethylene glycol and polypropylene glycol having a weight average molecular weight of about 600 grams/mole. Preferably, a hygroscopic compound is used. Exemplary hygroscopic compounds are glycerol and relatively low molecular weight polyols such as polyethylene glycol and polypropylene glycol having a weight average molecular weight of about 200 grams/mole. Host preferably, the external plasticizer is glycerol.

The external plasticizers may or may not be reactive or reacted with the required superabsorbent-polymer-forming materials. The plasticizer may be included in the above described reaction mixture. Alternatively, the superabsorbent polymer foam may be treated with the external plasticizer after formation of the foam, e.g., by spraying or immersion.

The specific amounts of external plasticizer may be selected by one having ordinary skill in the art to flexibilize the superabsorbent polymer foam to the extent desired. For example, where the plasticizer is included in the reaction mixture and is reactive with one or more of the superabsorbent-polymer-forming materials, the plasticizer may be used in a stoichiometrically excessive amount in order to obtain the desired flexibility. Alternatively, the external plasticizer may be added to the reaction mixture which is then reacted under conditions insufficient to cause full reaction of the plasticizer with the required superabsorbent-polymer-forming materials.

Where the substantially water-insoluble polymer material of the polymer foam is not crosslinked or only partially crosslinked, the foam may be further reacted so as to crosslink or further crosslink the polymer material. As noted above, some degree of crosslinking is necessary to render the polymer material superabsorbent. In addition, further crosslinking may also be desired in order to impart certain absorptive properties to a polymer foam which is already superabsorbent.

An uncrosslinked foam may result where the substantially water-insoluble polymer material comprises only the monomer in polymerized form, e.g., where the reaction mixture does not include an internal crosslinking agent or does include a latent crosslinking agent. Latent crosslinking agents may also result in partial crosslinking. By "latent crosslinking agent", it is meant that the crosslinking agent will not react under the particular conditions used for reacting the monomer and the internal crosslinking agent to form the water-insoluble polymer of the polymer foam. Thus, the previously described internal crosslinking agents may be used as latent crosslinking agents as long as the reaction conditions are selected so as to ensure latent reaction. However, the reaction mixture will preferably include at least one internal crosslinking agent which is reacted to form the substantially water-insoluble polymer material.

Where a latent crosslinking agent has been used, the foam may be subjected to conditions of time and temperature so as to react the latent crosslinking agent into the polymer network of the substantially water-insoluble polymer material of the foam. Although the required reaction conditions will vary, for example, with the particular chemistry involved, the reaction generally involves heating of the foam at temperatures of from about 100° C. to about 250° C. for a time of about 1 minute to about 30 minutes. Such reaction typically causes network crosslinking in substantially all of the polymer material of the foam. As a result, it typically increases the gel strength (and decreases the gel volume) of substantially all of the polymer material of the foam.

Partial crosslinking may also result from the reaction of only a portion of the monomer reactive sites with the internal crossl inking agent, due, for example, to a stoichiometric deficiency of internal crossl inking agent in forming the substantially water-insoluble polymer foam. The polymer material of such a foam (which may already be superabsorbent) can be further crosslinked after formation of the foam by reaction of the polymer material with a suitable external crosslinking agent. External crosslinking results in crossl inking of the polymer material of the foam surfaces in contact with the crosslinking agent, and depending on the reaction conditions, the subsurface polymer material. In general, the more extreme the conditions or reactive the reactants, the more surface and subsurface polymer material will be crosslinked. Crosslinking can be caused through various depths of the polymer material of the polymer foam, from the polymer surfaces in contact with the external crosslinking agent into the interior of the polymer material. In addition, zones of different crosslink densities can be prepared, e.g., by causing crosslinking in a stepwise manner. Thus a crosslink gradient can be formed with the highest crosslink density being toward the polymer surfaces (including those of the intercommunicating channels). In a preferred embodiment, only the surfaces of a foam formed of superabsorbent polymer material are further crosslinked such that the foam surfaces, including the surfaces of the intercommunicating channels, have relatively high gel strengths while the gel strength and gel volume of the subsurface polymer material is generally unchanged. Without wishing to be bound by theory, it is believed that such crosslinking may provide a gel strength sufficient to provide surface dryness of the foam when wetted (and therefore skin dryness in use) without significant adverse impact on the osmotic absorptive capacity and rate. In addition, such surface crosslinking may enhance the capillary absorptive rate.

Suitable external crosslinking agents include those described herein in reference to the internal crossl inking agent. Preferably, the external crosslinking agent is capable of forming covalent crosslink bonds with the polymer material of the foam, i.e., the external crossl inking agent contains one or more functional groups or unsaturated groups that are reactive with the polymer material of the foam. Where the substantially water-insoluble polymer material contains carboxylic acid groups, the preferred embodiment of covalent crosslinking generally occurs as a result of the formation of ester, amide, imide or urethane groups by reaction of the carboxylic acid groups with the corresponding functional group of the crosslinking agent. Accordingly, preferred crosslinking agents include polyhydroxy compounds, polyamines, polyisocyanates, polyamides, polyepoxides and hydroxyepoxide compounds. Preferably, the external crosslinking agent is a polyhydroxy compound, e.g., polyethylene glycol, polypropylene glycol, and glycerol. Most preferably, glycerol is used.

The polymer foam can be reacted with the external crosslinking agent by first exposing the foam to the external crosslinking agent, by, for example, spraying, immersion, or vapor deposition. The polymer material of the foam is then reacted with the external crosslinking agent under conditions of time and temperature sufficient to cause the reaction to the extent desired, depending on the particular polymer material and external crosslinking agent. Such conditions may be readily determined by one skilled in the art. Depending on the reaction chemistry, the crosslinking reaction may occur spontaneously upon contacting the polymer foam with the crosslinking agent, but generally has to be induced by, for example, irradiation or heating. Therefore, the external crosslinking agent will be chosen with consideration given to the method of induction.

Some of the external crosslinking agents, such as polyhydroxy compounds, can also serve as external plasticizers. In general, any external crosslinking agent of this type which is not fully reacted into the superabsorbent polymer material will serve as an external plasticizer. This can be achieved by using a stoichiometric excess of external crosslinking agent to polymer material, or by controlling the external crosslinking reaction conditions so as to avoid complete reaction of the crosslinking agent with the polymer material. In addition, the water which may be attracted by a hygroscopic crosslinking agent, for example, glycerol, may act to plasticize the superabsorbent polymer foam.

The resultant superabsorbent polymer foams of the invention can be characterized by various absorbency, structural, mechanical and other properties as follows:

ABSORBENCY CHARACTERISTICS

Absorptive capacity refers to the capacity of the superabsorbent polymer foam to absorb and retain fluids with which it comes into contact. Absorptive capacity of the foams herein can be considered to have two components: an osmotic absorptive capacity (i.e., gel volume) and a capillary absorptive capacity. The osmotic absorptive capacity refers to the ability of the polymer material of the foam to absorb fluids, whereas the capillary absorptive capacity refers to the ability of the foam channels to absorb fluids (e.g., by wicking). Similarly, the foams herein have an osmotic absorptive rate (the rate at which the polymer material absorbs fluids) and a capillary absorptive rate (the rate at which the channels absorb fluids). Unless otherwise specified, as used herein the absorptive capacity and rate refer to the total (i.e., combined osmotic and capillary) absorptive capacity and rate.

Absorptive capacity can vary significantly with the nature of the fluid being absorbed and with the manner in which fluid contacts the foam. For purposes of this invention, absorptive capacity is defined in terms of the amount of synthetic urine absorbed by any given superabsorbent polymer foam material in terms of grams of synthetic urine per gram of foam in a procedure hereinafter defined (since the specific gravity of the synthetic urine is approximately 1.0, absorptive capacity can also be reported in terms of ml of synthetic urine per gram of foam).

The superabsorbent polymer foams of the present invention are those which have an absorptive capacity of at least about 10 grams, more preferably at least about 15 grams, most preferably at least about 50 grams, of synthetic urine per gram of foam. Superabsorbent polymer foams having this relatively high absorptive capacity characteristic are especially useful in absorbent structures and articles since the foams can, by definition, hold desirably high amounts of discharged body fluids such as urine.

The absorptive rate is the absorptive capacity measured as a function of time. The absorptive rate, in grams (g) of synthetic urine per gram of superabsorbent polymer foam per second (sec), is preferably at least about 0.5 g/g/sec, more preferably at least about 1 g/g/sec, most preferably at least about 2 g/g/sec.

Absorptive capacity and rate can be determined for any given foam sample using the procedure described in the TEST METHODS section.

In addition to a relatively high absorptive capacity and absorptive rate, the superabsorbent polymer foams preferably also possess certain gel strength characteristics. Gel strength refers to the propensity of the foam to deform or spread under stress once the foam absorbs fluid. Without wishing to be bound by theory, it is believed that, for a given superabsorbent polymer material and gel strength, the capillary absorptive capacity and the capillary and osmotic absorptive rates may be increased by increasing the surface area to mass ratio of the foam. Therefore, it is desirable to utilize in absorbent structures and articles those superabsorbent polymer foams having an adequate gel strength and the greatest achievable surface area to mass ratio.

It has also been found that gel strength (i.e., gel deformation tendency) correlates directly with the shear modulus of the superabsorbent polymer foam. Accordingly, superabsorbent polymer foams having sufficient gel strength to be useful in absorbent structures and articles of the present invention can be appropriately characterized by specifying gel strength in terms of the shear modulus of the foam.

Shear modulus can be conventionally measured, for example, by a procedure which involves the use of a stress rheometer to determine the ratio of (a) stress applied to a given foam sample to (b) the resultant strain exhibited by the sample. The foam sample tested in this manner is swollen to its absorptive capacity with synthetic urine. The stress to strain ratio is determined, and the shear modulus of the resultant foam sample in dynes/cm$^2$ is then subsequently calculated from this ratio. A suitable procedure for use herein is described in U.S. Pat. No. Re. 32,649 issued to Brandt et al. on Apr. 19, 1988, incorporated herein by reference.

The superabsorbent polymer foams of the present invention preferably have gel strengths such that these foams exhibit a shear modulus of at least about 1 dyne/cm$^2$, more preferably within the range of from about 1 dyne/cm$^2$ to 5 dynes/cm$^2$. Without being bound by any particular theory, it is believed that foams having such gel strengths will resist deformation upon fluid absorption and will have a reduced tendency to flow (i.e., the foams are "fluid stable"). Thus, the preferred gel strengths may allow the intercommunicating channels of the foams of the present invention to be maintained and enlarged when swollen by fluids so that the foam may acquire and transport subsequent loadings of fluids. The preferred gel strengths may also serve to enhance skin dryness.

Another feature of the foams of the present invention is that the foams swell generally isotropically, even under moderate confining pressures, when fluids are deposited onto or come into contact with the foams. Isotropic swelling is used herein to mean that the foam swells generally equally in all directions when wetted. Isotropic swelling is an important property of the foam because the superabsorbent polymer material of the foam, cells, and intercommunicating channels are able to maintain their relative geometry and spatial relationships even when swollen such that the existing capillary channels are maintained, if not enlarged, during use (the polymer material, cells and channels get larger during swelling). Thus, the foam can imbibe and/or transport through itself additional loadings of fluid.

STRUCTURAL FEATURES

Specific, somewhat interrelated and interdependent structural properties of the superabsorbent polymer foams have been identified as being highly desirable in applications involving absorption of aqueous body fluids. The several structural properties of the preferred superabsorbent polymer foams can be summarized as follows:

A) SURFACE AREA TO UNIT MASS RATIO

The surface area to unit mass ratio is the total area of the superabsorbent polymer material surfaces of the foam, including the surfaces of the cells and intercommunicating channels, to the total mass of the superabsorbent polymer material. The surface area to mass ratio is indicative of the rate of fluid uptake, particularly the osmotic absorptive rate, of the foam. The greater the surface area to mass ratio of the foam, the more area there is for diffusion of the fluid to be absorbed. Thus, for foams having a given gel strength characteristic, foams having a higher surface area to mass are preferred.

The surface area to mass ratio is also believed to be important in minimizing deactivation of the superabsorbent material of the Foam by body fluids containing high molecular weight components, e.g., blood and menses. If the surface area to mass ratio is too small, such components, due to their molecular size, are believed to physically deactivate the foam or portions thereof.

For the above reasons, it is desirable to maximize the surface area to mass ratio of the superabsorbent polymer foams of the present invention. In general, any feature which increases foam capillarity will also increase the surface area to mass ratio. For example, surface area to mass increases as the cell size decreases and/or as the number of cells, percent open cells, and/or percent intercommunicating channels increases. Thus, the surface area to mass ratio may be increased by any of the foam composition or processing parameters which so influence these parameters.

The superabsorbent polymer foams herein will typically have a surface area to mass ratio of at least about 0.2 $m^2$/gram, more preferably at least about 1.6 $m^2$/g, and most preferably at least about 3 $m^2$/gram. A suitable method for determining the surface area to mass ratio (using the Brunauer-Emmet-Teller (BET) gas adsorption method) is set forth in greater detail in the TEST METHODS section.

B) PERCENT OPEN CELLS

Polymeric foams may be relatively closed-celled or relatively open-celled in character, depending upon whether and/or the extent to which, the cell walls or boundaries (i.e., the cell windows) are filled or taken up with polymeric material. The superabsorbent polymer foams of the present invention are relatively open-celled in that the individual cells of the foam are for the most part not completely isolated from each other by polymeric material of the cell walls. Thus, the cells in such substantially open-celled foam structures have intercellular openings or "windows" which are large enough to permit ready fluid transfer from one cell to the other within the foam structure. An open-celled structure is important for both the capillary absorptive rate and capacity of the foam. Improved capillary transport al so improves the osmotic absorptive rate since a greater area of the superabsorbent polymer material of the foam is exposed to the fluid.

In substantially open-celled structures of the type useful herein, the foam will generally have a reticulated character with S the individual cells being defined by a plurality of mutually connected, three dimensionally branched webs. The strands of polymeric material which make up the branched webs of the open-cell foam structure can be referred to as "struts." For purposes of the present invention, a superabsorbent foam is "open-celled" if at least about 25%, preferably at least about 50%, and most preferably at least about 75% of the cells in the foam structure are in fluid communication with at least one adjacent cell. Alternatively, the foam may be considered to be substantially open-celled if it has an available pore volume which exceeds a minimum value as set forth hereinafter.

In addition, the intercellular openings of the foams herein are such that the foam has substantially continuous, intercommunicating channels substantially throughout the foam network, i.e., the intercellular openings form an interconnecting network of channels which are free of polymer material such that the foam is liquid permeable. The channels allow fluids contacting the foam to be transported via capillary forces (i.e., capillary transport channels are formed) to other portions of the foam so that the total volume of the foam is used in absorbing the fluids. Further, when swollen, the cells and the intercommunicating channels allow fluids to pass through the foam either to superabsorbent polymer material remote from the initial point of fluid contact or to other structures in contact with the foam. Thus, the foam is considered to be fluid permeable due to the cells and the intercommunicating channels. The intercommunicating channels are believed to enhance the capillary absorptive rate and capacity. Since the channels allow distribution of fluids throughout the foam, they also provide increased utilization of the fluid-retentive properties of the superabsorbent polymer of the foam, thereby enhancing the osmotic absorptive rate of the foam.

Preferably, the intercellular openings are such to allow intercellular capillary flow of fluids (i.e., intercellular fluid communication) among at least about 25%, more preferably at least about 50% percent, most preferably at least about 75% percent, of the cells. The surface area to mass ratio and the available pore volume may be indicative of the level of cells having intercellular communication.

Features which influence the formation of intercommunicating channels include the level, particle size, and particle size distribution of the blowing agent and control of the expansion and reaction steps so as to expand the blowing agent prior to the critical viscosity.

C) AVERAGE CELL SIZE AND CELL SIZE DISTRIBUTION

Another structural feature of the superabsorbent polymer foams herein is cell size. Foam cells will frequently be substantially spherical in shape. Thus, the size or "diameter" of such substantially spherical cells is a commonly utilized parameter for characterizing foams in general, as well as for characterizing the preferred superabsorbent polymer foams of the present invention. Since cells in a given sample of polymeric foam will not necessarily be of approximately the same size, an average cell size, i.e., average cell diameter, will often be specified. Similarly, a cell size distribution reflecting the range of cell sizes may be specified.

Since cell size is a factor that determines the capillarity of the foam, cell size is a parameter that can directly affect both the osmotic and capillary absorptive rates of the superabsorbent foams herein. Cell size, in conjunction with the number of cells (which relates to density) may also affect mechanical properties, including flexibility, of the foams herein. In general, for a given density, the overall flexibility of the bulk foam may increase as the average cell size decreases.

Figure 2:
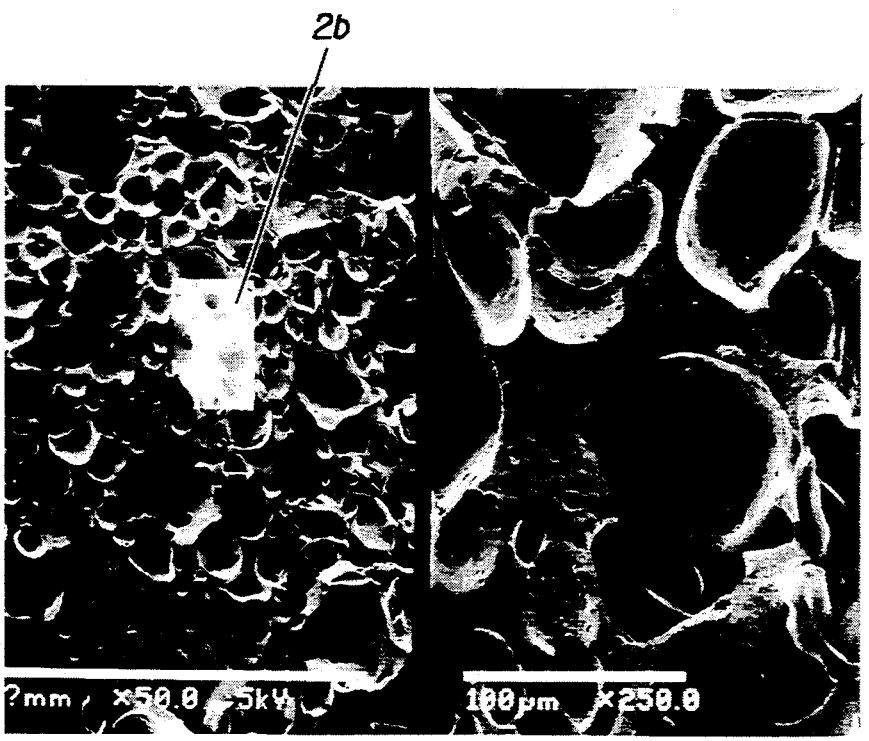
FIG. 2 is a photomicrograph showing a top view of an edge of the superabsorbent polymer foam in FIG. 1 taken from a plane perpendicular to the plane of the edge in FIG. 1, enlarged approximately 50 times, and also a portion of this view enlarged approximately 250 times.

A number of techniques are available for determining average cell size in foams. These techniques include mercury porosimetry methods which are well known in the art. The most useful technique, however, for determining cell size in foams involves simple photographic measurement of a foam sample. FIG. 1 of the drawings, for example, is a photomicrograph of an edge of a typical superabsorbent foam of the present invention. Superimposed on the portion of the photomicrograph marked 1a (the edge enlarged about 50 times) is a scale representing a dimension of 50 mm; on the portion marked 1b (a rectangular portion of 1a enlarged about 250 times) a scale representing a dimension of 100 microns (Similarly, FIG. 2, a photomicrograph of an edge of the foam of FIG. 1 taken from a plane perpendicular to the plane of the edge in FIG. 1, has similar scales superimposed on the portions marked 2a (50X) and 2b (250X)). Such scales can be used to determine average cell size via an image analysis procedure. Image analysis of photomicrographs of foam samples is a commonly employed analytical tool which can be used to determine average cell size of the foam structures herein. Such a technique is described in greater detail in U.S. Pat. No. 4,788,225 issued to Edwards et al. on Nov. 29, 1988, incorporated herein by reference. From the various cell measurements which are taken in determining average cell size, a cell size distribution can be easily determined, including range and size percentages within such range.

It is generally desirable to provide foams having the minimum possible cell size consistent with obtaining the intercellular fluid communication and surface area to mass ratio previously described. As determined by direct photographic measurement, the superabsorbent polymer foams of the present invention will typically have an average cell size of less than about 100 microns, more preferably less than about 50 microns, most preferably less than about 20 microns. Generally the minimum cell size will be in the range of from about 1 to about 10 microns. Preferably, at least about 50%, more preferably at least about 75%, most preferably at least about 90%, of the cells will lie within the above cell size ranges.

The cell size distribution may affect both the osmotic and capillary absorptive rates. For maximizing the capillary absorptive rate it is believed preferable to provide a narrow cell size distribution, preferably such that the foam has a cell distribution value of at most 5, more preferably at most 3, still more preferably at most 2. For the fastest capillary absorptive rate, the cell distribution value is preferably 1 (i.e., all cells are of the same size). Cell size distributions corresponding to these values are summarized in Table I. It is further believed that the osmotic absorptive rate is maximized with a foam morphology having combination of small cells and a wider cell size distribution such that there is "packing" of smaller cells among larger cells. Therefore, for a suitable balance of both osmotic and capillary absorption by the foams herein it is preferred that the cell distribution value be greater than 1 and less than 3, most preferably less than 2.

The size of the cells in the superabsorbent polymer foams can be influenced and controlled by variation of certain foam composition and processing features as described herein, particularly those which influence the particle size of the blowing agent in the stable dispersion. For example, the cell size is influenced by the viscosity ratio, the shear stress in forming the dispersion, and the temperature and pressure used in the expansion and reaction steps. For sufficiently flexible foams, cell size may also be altered by simply compressing the solid foam structures after they have been prepared.

A narrow cell size distribution may be promoted by proper selection of a surfactant for a given blowing agent and reaction mixture so as to minimize coalescence of the dispersed blowing agent particles before and/or during expansion. For example, a surfactant containing hydrophilic and hydrophobic groups is generally effective for stabilizing a water-insoluble blowing agent in a reaction mixture in which the solvent is water. The ratio of hydrophilic and hydrophobic groups in the surfactant can be varied to minimize coalescence of the blowing agent particles, preferably by matching the HLB values of the surfactant and the blowing agent, thereby promoting a uniform cell size distribution. A narrow cell size distribution may also be promoted by decreasing the viscosity ratio.

TABLE I

| Average Cell Size | Cell Distribution Value* | | | | |
|---|---|---|---|---|---|
| | 1 | 2 | 3 | 4 | >5 |
| 100 microns | 100% - 100 | 50% - 95–105 | 33.3% - 95–105 | 25% - 95–105 | 17% - 95–105 |
| | | 25% - 75–<95 | 33.3% - 65–<95 | 37.5% - 62–<95 | 41.5% - <95 |
| | | 25% - >105–125 | 33.3% - >105–135 | 37.5% - >105–138 | 41.5% - >105 |
| 50 microns | 100% - 50 | 50% - 45–55 | 33.3% - 45–55 | 25% - 45–55 | 17% - 45–55 |
| | | 25% - 35–<45 | 33.3% - 35–<45 | 37.5% - 33–<45 | 41.5% - <45 |
| | | 25% - >55–65 | 33.3% - >55–65 | 37.5% - >55–65 | 41.5% - >55 |
| 20 microns | 100% - 20 | 50% - 18–22 | 33.3% - 18–22 | 25% - 18–22 | 17% - 18–22 |
| | | 25% - 15–<18 | 33.3% - 15–<18 | 37.5% - 12–<18 | 41.5% - <18 |
| | | 25% - >22–25 | 33.3% - >22–25 | 37.5% - >22–26 | 41.5% - >22 |

*Percent of cells having specified size, in microns (e.g., 25% - >105–125 means that 25% of the cells have a size of greater than 105 microns and less than or equal to 125 microns).

D) FOAM DENSITY

Density of the superabsorbent polymer foams may influence a number of performance and mechanical characteristics of these foams. Such characteristics include both the osmotic and capillary absorptive capacities and rates, and foam flexibility. In general, for a given surface area to mass ratio and cell size, as the foam density decreases, the osmotic absorptive rate and capillary absorptive capacity will increase. Importantly, the density of the superabsorbent polymer foams can also determine the cost effectiveness of the absorbent articles herein.

Foam density (in grams of foam material per cubic centimeter of foam volume in air) is specified herein on a dry basis. Thus the amount of any absorbed aqueous liquid, e.g., any residual liquid which may be left in the foam, for example, after its formation, is disregarded in calculating and expressing foam density. Foam density as specified herein does include, however, any residual solid material such as surfactant, external plasticizer, etc., which may be present in the superabsorbent polymer foam. Such residual material may, in fact, contribute significant mass to the foam material.

Any suitable gravimetric procedure which will provide a determination of mass of solid foam material per unit volume of foam structure can be used to measure foam density. For example, a gravimetric procedure suitable for use herein is described more fully in U.S. Pat. No. 5,147,345 issued to Young et al. on Sep. 15, 1992. This patent is incorporated herein by reference. For those situations where the foam sample preparation procedures (drying, aging, preflexing, etc.,) might inadvertently alter the density measurements obtained, then alternate density determination tests may also be utilized. Such alternative methods, for example, might include gravimetric density measurements using a test liquid absorbed within the foam material. This type of density determination method can be useful for characterizing very low density foams such as the foams herein wherein the dry density approximates the inverse of the pore volume of the foam. See Chatterjee, "Absorbency," *Textile Science and Technology*, Vol. 7, 1985, p. 41, incorporated herein by reference. The ranges for foam density set forth hereinafter are intended to be inclusive, i.e., they are intended to encompass density values that may be determined by any reasonable experimental test method.

It is generally preferred to minimize the density of the superabsorbent polymer foams consistent with obtaining a foam which has a desired structure of intercommunicating channels, cell size, and surface area to mass ratio. Foam density can be adjusted by controlling certain foam composition and processing parameters, for example, the addition level of the blowing agent. The superabsorbent polymer foams of the present invention will typically have dry basis density values which range from about 0.1 to about 0.5 g/cm$^3$. Density of the superabsorbent polymer foams herein need not be uniform throughout the structure; i.e., some portions or zones of the foam may have relatively higher or lower densities than other portions or zones thereof. However, where the foam has substantially continuous intercommunicating channels substantially throughout and a relatively small cell distribution value, the density will be substantially uniform throughout.

E) PORE VOLUME

As stated above, for very low density foams, dry density approximates the inverse of the pore volume. Therefore, pore volume may serve to provide density measurements for the foams herein. In addition, pore volume can be correlated to the number of cells, the percentage of open cells, and the percentage of intercommunicating channels in the foam structure. In general, as the pore volume increases, the number of cells, number of open cells, and the degree of fluid intercommunication of foam channels also increases.

Pore volume is a measure of the volume of the openings or cells in a porous foam structure per unit mass of solid material (i.e., polymer structure plus any residual solids) which forms the foam structure. Pore volume can be important in influencing a number of performance and mechanical features of the superabsorbent foams such as described in reference to the foam density.

Pore volume can be determined by any suitable experimental method which will give an accurate indication of the actual pore volume of the structure. Such experimental methods will generally involve the measurement of the volume and/or mass of a test liquid which can be introduced into the foam structure and which therefore is representative of the volume occupied by the open cells of the foam. For this reason the pore volume parameter of the foams may also be referred to as "available pore volume."

One conventional way for determining available pore volume experimentally involves the introduction of a low surface tension liquid such as isopropanol into the foam structure from outside the foam structure. A procedure for determining available pore volume using isopropanol is set forth in the above referenced U.S. Pat. No. 5,147,345. It should be understood, however, that alternative test liquids and procedures may also be used to determine available pore volume.

It is generally desirable to maximize the pore volume of the foams herein. The pore volume of the superabsorbent polymer foams can be influenced and controlled by adjusting many of the same foam composition and processing parameters as for density adjustment. For example, pore volume influencing features may include the blowing agent addition level and blowing agent particle size.

The superabsorbent polymer foams of the present invention will generally have a pore volume of at least about 5 ml/g, more preferably at least about 10 ml/g, and most preferably at least about 30 ml/g. Typically the pore volume will range from about 5 to about 40 ml/g. Such ranges for pore volume are intended to be an "inclusive" definition of theoretical pore volume for the foams encompassed by this invention. Thus if any experimental method which can reasonably be expected to give measurements approximating theoretical pore volume provides values within the foregoing ranges, then the foam materials tested by any such method are within the scope of this invention.

F) CAPILLARY SUCTION SPECIFIC SURFACE AREA

Another structural feature of the preferred superabsorbent polymer foams herein is a certain capillary suction specific surface area. Capillary suction specific surface area is, in general, a measure of the test-liquid-accessible surface area of the polymeric network forming a particular foam per unit mass of the bulk foam material (i.e., polymer structural material plus solid residual material). Capillary suction specific surface area is determined both by the dimensions (i.e., diameter) of the cellular units in the foam and by the size (i.e., length, width and thickness) of the struts which form cellular units. Capillary suction specific surface area is thus a way of quantifying the total amount of solid surface provided by the foam network to the extent that such a surface participates in absorbency.

The capillary suction specific surface area of an open-celled foam structure such as the superabsorbent polymer foams of the present invention is a feature of the foam that influences the capillarity (or capillary suction) exhibited by the foam. Although the foam surface area to mass ratio is particularly important for determining the osmotic absorptive rate of the foam, the foam capillarity may be selected and controlled such that the superabsorbent polymer foams have a degree of capillarity allowing transport, e.g., by wicking, of fluids within the foam structure. Adjustment of capillary suction specific surface area is thus a suitable means for providing a degree of capillarity for the superabsorbent polymer foams as may be desired. Foams of relatively high capillary suction specific surface area may provide a very desirable combination of high capillary absorptive capacity and high capillary and osmotic absorptive rates. High specific surface area is a consequence of the fineness of the struts making up the foam structure.

The capillary suction specific surface area of the superabsorbent foams is influenced and controlled by adjusting many of the same composition and processing parameters which affect the foam density and pore volume.

For purposes of this invention, the specific surface area of any given superabsorbent polymer foam material can and will usually be determined by a procedure which involves the principle of capillary suction. In such a procedure, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method which is suitable for use herein is set forth in the above referenced U.S. Pat. No. 5,147,345. Any reasonable alternative method for determining capillary suction specific surface area may also be utilized.

The superabsorbent polymer foams herein preferably have a capillary suction specific surface area of at least about $0.1$ m$^2$/g, more preferably at least about $0.5$ m$^2$/g, most preferably at least about $1$ m$^2$/g. Typically the capillary suction specific surface area will be in the range of about $0.1$ to about $5$ m$^2$/g. Superabsorbent foams having the above capillary suction specific surface area values may possess an especially desirable balance of capillary and osmotic absorptive capacities and rates for aqueous body fluids such as urine.

MECHANICAL FEATURES

The superabsorbent polymer foams preferably possess mechanical properties, e.g., flexibility, integrity, softness, etc., which render such foams especially suitable for use in absorbent articles such as disposable diapers.

The superabsorbent foams of the present invention are preferably flexible when intended for use in absorbent articles. By "flexible" it is meant that the foam material can be used in or as an absorbent member which will conform to the general shape and contours of the human body. In general, flexible foams can be deformed or bent to the extent necessary for use in such absorbent articles without significant damage to their structural integrity or significant loss of their absorbent properties.

The superabsorbent polymer foams herein are also preferably sufficiently flexible to withstand compressive or deforming forces which are encountered during preparation, processing, packaging, shipping and storing of absorbent articles containing such foam materials. Disposable diapers, for example, are generally packaged and marketed in a folded condition wherein the diaper core is folded in both the longitudinal and transverse directions. Disposable diapers are also generally marketed in the form of stacks of folded diapers, which stacks are contained and compressed by their surrounding packaging. Accordingly, the compressive and deforming forces to which the superabsorbent polymer foam may be subjected during processing and marketing may be even greater than those which are applied to the foam materials in use.

Given the nature of treatment which the superabsorbent polymer foams herein must generally withstand, preferred foam materials of this invention will possess flexibility characteristics which can be quantified by referencing their ability to withstand bending without undergoing significant damage to their structural integrity. Described in the TEST METHODS section is a procedure for determining the flexibility of the foams herein by determining whether and how many times a foam sample of a given specified size can be bent around a cylindrical mandrel at a specified rate without breaking. Particularly preferred foams of the invention are those which are flexible enough so that, at their point of use as an absorbent for body fluids, the (synthetic urine) saturated foam material at 37° C. can be subjected to this bending test without breaking (i.e., the foams exhibit a bending value of at least one cycle). More preferably, the foams can be bent at least 2 times, most preferably at least 5 times, without breaking when subjected to such a test procedure.

The superabsorbent polymer foams of the present invention preferably possess the additional mechanical attributes of structural integrity in use and softness (i.e., lack of irritation) to the touch. For example, superabsorbent polymer foams that will be employed in such absorbent articles as infant diapers will frequently be subjected to both dynamic and static forces when the wearer walks, runs, crawls or jumps. Such forces may tend to rip or tear or otherwise fragment the foam structure. Thus, it would be advantageous for foams (particularly foam sheets) which are to be used in this manner to have sufficient structural integrity to minimize the incidence of foam tearing or fragmenting in use.

The superabsorbent foams may also be used in absorbent articles in configurations wherein the foam material surface may come into close proximity to the wearer's skin. Accordingly, it would be very desirable for the surface of the superabsorbent foams herein to be acceptably soft and non-irritating to the touch.

MISCELLANEOUS PROPERTIES

For use as fluid absorbents in absorbent articles, the superabsorbent polymer foams herein preferably possess relatively low levels of extractable polymer material. It is believed that polymer material extracted by body fluid once the superabsorbent polymer material of the foam forms a hydrogel can alter both the chemical and physical characteristics of the body fluid to the extent that such fluid is more slowly absorbed and more poorly held by the superabsorbent polymer foam containing absorbent article. Such effects are described in the above referenced U.S. Pat. No. Re. 32,649. As a result, leaching of polymer into the body fluid to be absorbed can result in less efficient utilization of the superabsorbent polymer foam in the absorbent articles and a greater incidence of undesirable leakage of body fluid from the article.

Extractable polymer levels of the superabsorbent polymer foams herein can be determined by contacting a sample of the foam with a synthetic urine solution for the substantial period of time (e.g., at least 16 hours) which is needed to reach extraction equilibrium, by then filtering the swollen foam material from the supernatant liquid, and finally by then determining the polymer content of the filtrate. Such a method for determining the extractable polymer content for carboxylic and sulfonic acid based superabsorbent polymer materials which is suitable for use herein is described in the above referenced U.S. Pat. No. Re. 32,649.

Preferred superabsorbent polymer foams of the present invention possess two types of extractable polymer content characteristics. It is believed that both the total amount of extractable polymer in the foam and the rate at which such extractable material is leached are important with regard to the absorptive performance of the superabsorbent polymer foam. Accordingly, the superabsorbent polymer foams herein preferably have an initial extractable polymer content, i.e., the level of extractable polymer which is removed after one hour in contact with synthetic urine, of no more that about 7.5% by weight, more preferably no more than about 5% by weight of the foam. In addition, the foams preferably also have an equilibrium extractable polymer content, i.e., the equilibrium level of extractable polymer removed after, for example, sixteen hours in contact with synthetic urine, of no more than about 17% by weight, more preferably no more than about 10% by weight of the foam sample.

In addition, preferred superabsorbent polymer foams of the present invention exhibit a particular relationship between absorptive capacity and equilibrium extractable polymer content, as described in the above referenced U.S. Pat. No. Re. 32,649. Such preferred foams can be prepared in accordance with the general teachings of U.S. Pat. Re. 32,649 which are pertinent to such polymer materials. For example, the extractable polymer content may be minimized by a controlled, minimum utilization of initiator (when used) and/or the use of relatively low temperatures for reaction of the monomer and/or internal crosslinking agent (e.g., from about 20° C. to about 80° C.).

APPLICATIONS

The superabsorbent polymer foams can be used for many purposes in many fields of use as are known in the foam art. The foams are particularly suitable for use in applications where it is desirable to absorb and/or retain fluids, for example, in absorbent articles; paper tissue (including toweling); packing containers; drug delivery devices; wound cleaning devices; burn treatment devices; ion exchange column materials; construction materials; agricultural or horticultural materials such as seed sheets or water-retentive materials; and industrial uses such as sludge or oil dewatering agents, materials for the prevention of dew formation, dessicants, and humidity control materials.

Because of the unique absorption properties of the foam, the superabsorbent polymer foam is especially suitable for use as an absorbent core material in absorbent articles, especially disposable absorbent articles. As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). An "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20 shown in FIG. 3. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, sanitary napkins, pantiliners, and the like.

Figure 3:
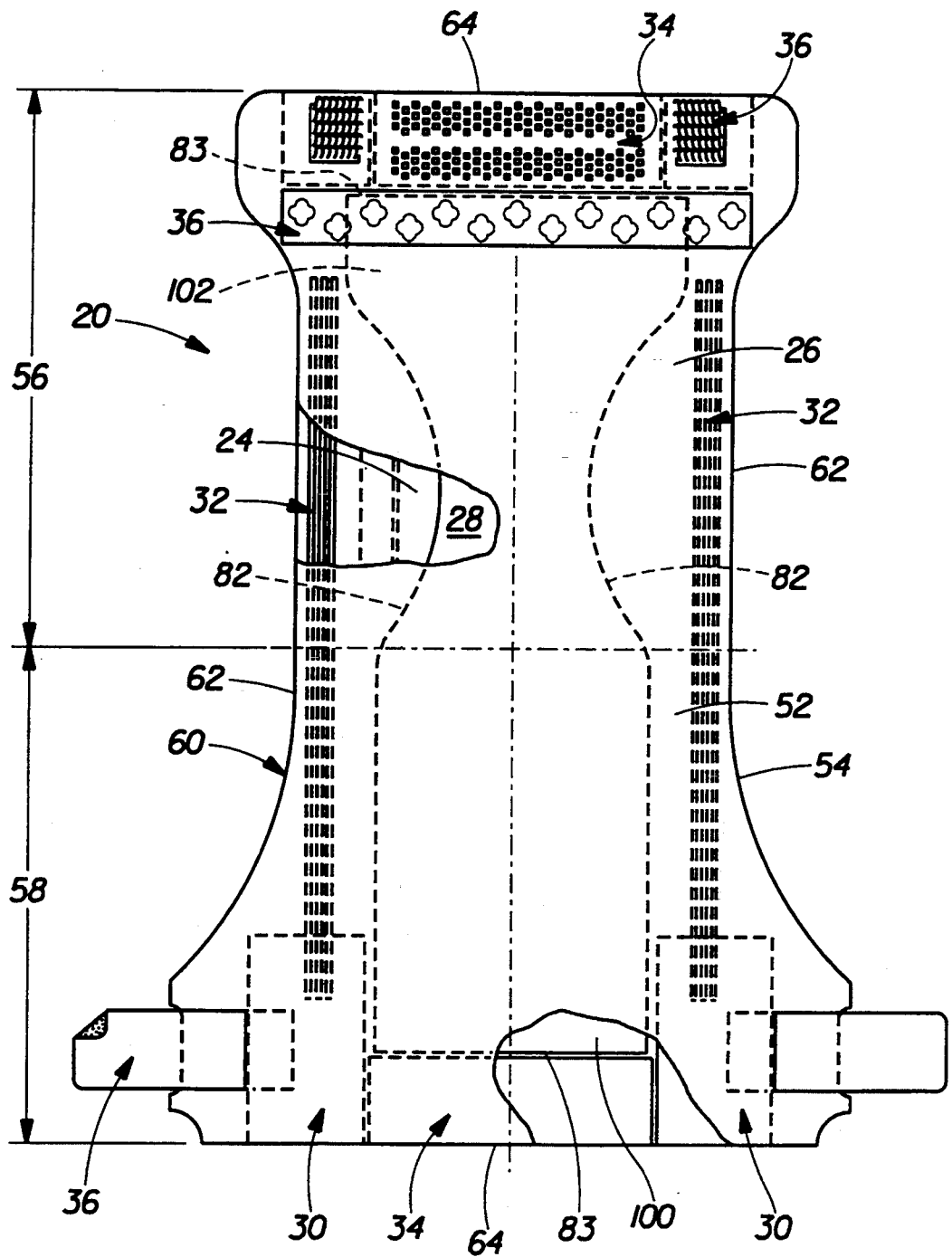
FIG. 3 is a plan view of a disposable diaper embodiment of the present invention having portions cut-away to reveal underlying structure, the outer surface of the diaper facing the viewer.

FIG. 3 is a plan view of the diaper 20 of the present invention in its flat-out, uncontracted state (i.e., with elastic induced contraction removed) with portions of the structure being cut-away to more clearly show the construction of the diaper 20 and with the portion of the diaper 20 which faces away from the wearer, the outer surface 52, oriented towards the viewer. As shown in FIG. 3, the diaper 20 preferably comprises a liquid pervious topsheet 24; a liquid impervious backsheet 26 joined with the topsheet 24; an absorbent core 28 (having a garment surface 100, a body surface 102, side edges 82, and waist edges 83) positioned between the topsheet 24 and the backsheet 26; elasticized side panels 30; elasticized leg cuffs 32; elastic waist features 34; and a fastening system 36.

The diaper 20 is shown in FIG. 3 to have an outer surface 52, an inner surface 54 opposed to the outer surface 52, a first waist region 56, a second waist region 58 opposed to the first waist region 56, and a periphery 60 which is defined by the outer edges of the diaper 20 in which the longitudinal edges are designated 62 and the end edges are designated 64. (While the skilled artisan will recognize that a diaper is usually described in terms of having a pair of waist regions and a crotch region between the waist regions, in this application, for simplicity of terminology, the diaper 20 is described as having only waist regions, each of the waist regions including a portion of the diaper which would typically be designated as part of the crotch region). The inner surface 54 of the diaper 20 comprises that portion of the diaper 20 which is positioned adjacent to the wearer's body during use (i.e., the inner surface 54 generally is formed by at least a portion of the topsheet 24 and other components joined to the topsheet 24). The outer surface 52 comprises that portion of the diaper 20 which is positioned away from the wearer's body (i.e., the outer surface 52 generally is formed by at least a portion of the backsheet 26 and other components joined to the backsheet 26).

FIG. 3 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 60 of the diaper 20. While the topsheet 24, the backsheet 26, and the absorbent core 28 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. Pat. No. 5,151,092, "Absorbent Article With Dynamic Elastic Waist Feature Having A Predisposed Resilient Flexural Hinge", which issued to Kenneth B. Buell, et al. on Sep. 29, 1992; each of which is incorporated herein by reference. Alternatively preferred configurations for disposable diapers herein are also disclosed in U.S. Pat. No. 4,808,178 entitled "Disposable Absorbent Article Having Elasticized Flaps Provided With Leakage Resistant Portions" issued to Mohammed I. Aziz and Ted L. Blaney on Feb. 28, 1989; U.S. Pat.

No. 4,695,278 entitled "Absorbent Article Having Dual Cuffs" issued to Michael I. Lawson on Sep. 22, 1987; and U.S. Pat. No. 4,816,025 entitled "Absorbent Article Having a Containment Pocket" issued to John H. Foreman on Mar. 28, 1989. These patents are incorporated herein by reference.

The topsheet 24 is positioned adjacent the body surface 102 of the absorbent core 28. The topsheet 24 is compliant, soft feeling, and non-irritating to the wearer's skin. Further, the topsheet 24 is liquid pervious, permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. There are a number of manufacturing techniques which may be used to manufacture the topsheet 24. For example, the topsheet 24 may be a nonwoven web of fibers, the web being spunbonded, carded, wet-laid, meltblown, hydroentangled, combinations of the above, or the like, A preferred topsheet is carded and thermally bonded by means well known to those skilled in the fabrics art, A preferred topsheet comprises a web of staple length polypropylene fibers such as is manufactured by Veratec, Inc., a Division of International Paper Company, of Walpole, Mass. under the designation P-8, The topsheet 24 may be joined to the absorbent core 28 and to the backsheet 26 by attachment means (not shown) such as those well known in the art, Suitable attachment means are described herein with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery 60 and are indirectly joined together by directly joining them to the absorbent core 28. The topsheet 24 or backsheet 26 may be directly Joined to the absorbent core comprising the superabsorbent foam by forming the foam on the topsheet material or backsheet material. Alternatively, e.g., where the absorbent core 28 is a free superabsorbent foam sheet or a foam-bearing structure (e.g., paper tissue comprising the superabsorbent foam), the topsheet or backsheet may be joined to the core by any attachment means such as are known in the art.

The backsheet 26 is positioned adjacent the garment surface 100 of the absorbent core 28. The backsheet 26 may be joined to the absorbent core 28 by forming the foam on the backsheet material or, e.g., where a free superabsorbent polymer foam sheet or other foam-bearing structure is used as the absorbent core 28, by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, more preferably several lines of adhesive filaments swirled into a spiral pattern such as is illustrated by the apparatus and methods shown in U.S. Pat. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet include RR8220 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26.

The absorbent core 28 is positioned between the topsheet 24 and the backsheet 26. The absorbent core 28 is generally compressible, conformable, non-irritating to the wearer's skin, and capable of absorbing and retaining liquids such as urine and other certain body exudates. As shown in FIG. 3, the absorbent core 28 has a garment surface 100, a body surface 102, side edges 82, and waist edges 83. The absorbent core 28 may be manufactured in a wide variety of sizes and shapes (e.g., rectangular, hourglass, "T"-shaped, asymmetric, etc.). As shown in FIG. 3, the absorbent core preferably has a modified T-shape. The absorbent core may include one or more layers of absorbent materials and a wide variety of liquid-absorbent materials commonly used in disposable diapers and other absorbent articles. The total absorbent capacity of the absorbent core 28 should, however, be compatible with the design loading and the intended use of the diaper 20. Further, the size and absorbent capacity of the absorbent core 28 may be varied to accomodate wearers ranging from infants through adults.

The absorbent core 28 comprises the superabsorbent polymer foam of the present invention. The superabsorbent polymer foam can be incorporated into the absorbent core 28 in any of the forms described herein (e.g., particulate, sheet form, or joined to a substrate) according to any conventional method. For superabsorbent foam in particulate form, the foam can be incorporated into the diaper in the same manner as conventional particulate superabsorbent or absorbent gelling materials. Alternatively, a free foam sheet, cut or formed to a desired size, may be incorporated as the absorbent core 28 or as one or more of the layers of the absorbent core. In still another embodiment, the superabsorbent foam is incorporated as formed on one or more of the diaper components (e.g., the topsheet 24, another absorbent core material such as a layer of tissue paper, or the backsheet 26), the diaper component serving as a permanent substrate (carrier). In a preferred embodiment, the superabsorbent polymer foam is formed on an absorbent carrier, more preferably a carrier providing fast wicking properties such as tissue paper, such that the composite absorbent material acts as the absorbent core.

The absorbent cores of the present invention may consist solely of one or more (a multiplicity of) layers of the superabsorbent polymer foam or foam-bearing carriers of the present invention; may comprise a combination of layers including the foams or foam-bearing carriers; or any other absorbent core configuration including one or more of the foams or foam-bearing carriers. Thus, the absorbent core can also comprise conventional absorbent core materials. Examples of other suitable absorbent materials are creped cellulose wadding; meltblown polymers including coform; chemically stiffened, modified or cross-linked cellulosic fibers; tissue, including tissue wraps and tissue laminates; conventional absorbent foams; absorbent sponges; conventional superabsorbent polymers and absorbent gelling materials (e.g., particulate, including fibrous, polymers or materials); or any equivalent material or combinations of materials.

The absorbent core preferably comprises a carrier web of fiber material and the superabsorbent polymer foam of the present invention. Such cores can be prepared by any process or technique which provides a fibrous carrier web and the foam. In a preferred embodiment, the absorbent core is formed by air-laying a substantially dry mixture of fibers, densifying the resultant web if desired or necessary, and then forming the superabsorbent foam on the web. The air-laid web will preferably comprise substantially unbonded fibers and will preferably have a moisture content of 10% or less. The foam can be formed by printing the stabilized dispersion on the web as desired and then expanding and reacting the dispersion so as to form the superabsorbent foam on the web. The foam can be present on the web in particular areas of the web and/or in a pattern so as to provide absorption properties designed for the intended use of the diaper 20. For example, the web having foam formed thereon can be designed according to the absorption requirements for boy and girl wearers. The web having the superabsorbent foam formed thereon can then be incorporated into the diaper 20 by any conventional method.

Various types of fiber material can be used in the carrier web. Any type of fiber material which is suitable for use in conventional absorbent products is also suitable for use in the carrier web. Specific examples of such fiber materials include cellulose fibers, modified cellulose fibers, rayon, polypropylene, and polyester fibers such as polyethylene terephthalate (DACRON), hydrophilic nylon (HYDROFIL), and the like. Other fiber materials include cellulose acetate, polyvinyl acetate, polyamides (such as nylon), bicomponent fibers, tricomponent fibers, mixtures thereof, and the like. Hydrophilic fiber materials are preferred. Examples of suitable hydrophilic fiber materials in addition to some already mentioned are hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent products, are suitable for use in the absorbent members of the present invention by virtue of their good wicking properties. This is because, in the structures herein, the wicking propensity of the fibers is as important, if not more important, than the absorbent capacity of the fiber material itself due to the high rate of fluid uptake of the superabsorbent polymer foams of the present invention which are included in the core. Hydrophobic synthetic fibers can also be used, but are less preferred.

For reasons of availability and cost, cellulose fibers are generally preferred for use herein as the hydrophilic fiber material of the absorbent core. Most preferred are wood pulp fibers which are also referred to as airfelt.

Other cellulosic fiber materials which may be useful in certain absorbent cores herein are chemically stiffened cellulosic fibers. Preferred chemically stiffened cellulosic fibers are the stiffened, twisted, curled cellulosic fibers which can be produced by internally cross-linking cellulose fibers with a crosslinking agent. Types of stiffened, twisted, curled cellulosic fibers useful as the hydrophilic fiber material of the absorbent cores herein are described in greater detail in U.S. Pat. No. 4,822,453 entitled "Absorbent Structure Containing Individualized, Crosslinked Fibers Having Reduced Residuals And Fibers Thereof", issued to Herron, at al. on Dec. 26, 1989; U.S. Pat. No. 4,889,597 entitled "Process For Making Wet-Laid Structures Containing Individualized Stiffened Fibers", issued to Bourbon, et al. on Dec. 26, 1989; and U.S. Pat. No. 4,898,642 entitled "Twisted, Chemically Stiffened Cellulosic Fibers And Absorbent Structures Made Therefrom", issued to Moore, et al. on Feb. 6, 1990. Each of these patents are incorporated herein by reference.

The relative amount of fiber material and superabsorbent polymer foam in the resultant web can be most conveniently expressed in terms of a weight percentage of the absorbent core. The absorbent cores preferably contain from about 2% to about 98%, more preferably from about 5% to about 75%, and most preferably from about 10%, to about 60%, by weight of the absorbent core, of the superabsorbent polymer foam. This concentration of the foam can be expressed in terms of a weight ratio of fiber to foam. This ratio may range from about 98:2 to about 2:98. For most absorbent cores, the optimum fiber-to-foam weight ratio is in the range of from about 95:5 to about 25:75, most preferably from about 90:10 to about 40:60.

In an alternative embodiment, the diaper 20 comprises a dual-layer absorbent core comprising an absorbent member and a sheet of the superabsorbent polymer foam of the present invention. Typically the foam sheet is positioned subjacent the absorbent member (i.e., between the absorbent member and the backsheet 26).

The absorbent member serves to quickly collect and temporarily hold discharged liquids and to transport such liquids by wicking from the point of initial contact to other parts of the absorbent member and to the foam sheet. The absorbent member preferably comprises a web or batt of fiber materials. Various types of fiber material can be used in the absorbent member such as the fiber materials previously described herein. Cellulosic fibers are generally preferred for use herein, wood pulp fibers being especially preferred. The absorbent member can also contain specific amounts of a particulate, absorbent, polymeric composition. The absorbent member, for example, can contain up to about 50% by its weight of the polymeric composition. In the most preferred embodiments, the absorbent member contains from 0% to about 8% by its weight of a particulate, absorbent, polymeric composition. In alternatively preferred embodiments, the absorbent member comprises chemically stiffened cellulostc fibers as previously described. Exemplary embodiments of the absorbent member useful in the present invention are described in U.S. Pat. No. 4,673,402 entitled "Absorbent Article With Dual-Layered Cores" which issued to Paul T. Weisman, et al. on Jun. 16, 1987; and U.S. Pat. No. 4,834,735 entitled "High Density Absorbent Members Having Lower Density and Lower Basis Weight Acquisition Zones" issued to Miguel Alemany, et el. on May 30, 1989. These patents are hereby incorporated herein by reference. Absorbent members having a storage zone and an acquisition zone having a lower average density and a lower average basis weight per unit area than the storage zone so that the acquisition zone may effectively and efficiently rapidly acquire discharged liquid are especially preferred for use herein.

The absorbent member can be of any desired shape, for example, rectangular, oval, oblong, asymmetric, or hourglass-shaped. The shape of the absorbent member may define the general shape of the resulting diaper 20.

The foam sheet of the present invention need not be the same size as the absorbent member and can, in fact, have a top surface which is substantially smaller or larger than the top surface area of the absorbent member. The foam sheet can be smaller than the absorbent member, for example, having a top surface area from about 0.10 to about 1.0 times that of the absorbent member. More preferably, the top surface area of the foam sheet will be only from about 0.10 to about 0.75, and most preferably, the top surface area of the foam sheet will be only from about 0.10 to about 0.5 times that of the absorbent member. Alternatively, the absorbent member is smaller than the foam sheet and has a top surface area from about 0.25 to about 1.0 times, more preferably from about 0.3 to about 0.95 times that of the foam sheet. In this alternative embodiment, the absorbent member preferably comprises chemically stiffened cellulosic fibers.

The foam sheet is preferably placed in a specific positional relationship with respect to the backsheet and/or the absorbent member in the diaper. More particularly, the foam sheet is positioned generally toward the front of the diaper so that the foam sheet is most effectively located to acquire and hold discharged liquids.

In alternatively preferred embodiments, a multiplicity of foam sheets, preferably from about two to about six foam strips or sheets, may be used. Further, additional absorbent layers, members, or structures may be placed into the absorbent core. For example, an additional absorbent member may be positioned between the foam sheet and the backsheet to provide reserve capacity for the absorbent core and/or a layer to distribute liquids passing through the foam sheet to other portions of the absorbent core or to the foam sheet. The foam sheet may also alternatively be positioned over the absorbent member so as to be positioned between the topsheet and the absorbent member.

In an alternative embodiment of the absorbent cores of the present invention, the absorbent core comprises a laminate (a layered absorbent core) containing at least one, and optionally two or more, layers of superabsorbent polymer foam particles of the present invention. The laminates preferably comprise layers or webs of fibrous materials such as previously described, preferably a sheet of absorbent material, such as tissue paper. Such layered absorbent structures are more fully described in U.S. Pat. No. 4,578,068 entitled "Absorbent Laminate Structure" issued to Timothy A. Kramer, et al. on Mar. 25, 1986, which patent is incorporated herein by reference. Additional methods and apparatus for making such laminates are described in U.S. Pat. No. 4,551,191 entitled "Method For Uniformly Distributing Discrete Particles On A Moving Porous Web", issued to Ronald W. Kock, et al. on Nov. 5, 1985, which patent is incorporated herein by reference.

The relative amount of fiber material and particulate superabsorbent polymer foam may be the same as previously described with respect to the foam formed on a carrier web. In addition, the foam particles may be dispersed in various weight ratios throughout different regions and thicknesses of the absorbent core. For example, the mixture of fiber material and the foam particles may be disposed only in certain portions of the absorbent core. Preferably, the absorbent core contains an uniformly distributed mixture of hydrophilic fiber material and the foam particles. The foam particles may be substantially uniformly dispersed (thoroughly dispersed) throughout the entire absorbent core as disclosed in U.S. Pat. No. 4,610,678 entitled "High-Density Absorbent Structures", issued to Weisman, et al. on Sep. 9, 1986, which patent is incorporated herein by reference. The foam particles may alternatively be distributed in regions or zones which have higher concentrations of the foam than do other regions or zones. For example, U.S. Pat. No. 4,699,823 issued to Kellenberger, et al. on Oct. 13, 1987, discloses an absorbent member having a particulate, absorbent, polymeric composition distributed in a positive gradient through at least a portion of the thickness of the absorbent member. Preferably, the concentration gradient along the thickness dimension has the lowest concentration at or near the surface of the absorbent member which receives liquids (i.e., the top surface) and the highest concentration at or near the back surface of the absorbent member. This patent is incorporated herein by reference.

An alternative embodiment of the layered absorbent cores of the present invention is a "pouch" containing the particulate, superabsorbent polymer foam. The pouch is a layered absorbent core as described above wherein the number of fibrous webs equals two. The fibrous webs are joined to each other around their periphery so as to form a large pocket in the middle of the pouch. The foam particles are encased between the fibrous webs in the pocket. Thus, the pouch is similar to a tea bag in that the foam particles are free to swell and absorb within the pouch. The fibrous webs of the pouch preferably comprise a nonwoven material as are known in the art with the nonwoven webs being heat sealed about their periphery, although other means for sealing the webs together as are known in the art, such as adhesives or ultrasonic bonds, may also be used.

The absorbent cores herein can contain a variety of optional materials in addition to the fiber materials and the superabsorbent polymer foam. Such optional materials can include, for example, fluid distribution aids, antimicrobials, pH control agents, odor control agents, perfumes, etc. If present, these optional components will generally comprise no more than about 30% by weight of the absorbent cores herein.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) The above referenced U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz, et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff comprising a barrier flap and a spacing elastic member such as described in the above referenced U.S. Pat. No. 4,909,803. In a preferred embodiment, each elasticized leg cuff 32 additionally comprises an elastic gasketing cuff with one or more elastic strands, positioned outboard of the barrier cuff such as described in the above referenced U.S. Pat. No. 4,695,278.

The diaper 20 preferably further comprises elastic waist features 34 that provide improved fit and containment. The elastic waist features 34 at least extend longitudinally outwardly from the waist edges 83 of the absorbent core 28 and generally form at least a portion of the end edges 64 of the diaper 20. Thus, the elastic waist features 34 comprise that portion of the diaper at least extending from the waist edges 83 of the absorbent core 28 to the end edges 64 of the diaper 20 and is intended to be placed adjacent the wearer's waist. Although disposable diapers are generally constructed so as to have two elastic waist features, one positioned in the first waist region and one positioned in the second waist region, diapers can be constructed with a single elastic waist feature encircling the wearer. Further, while the elastic waist features or any of their constituent elements can comprise a separate element affixed to the diaper 20, the elastic waist features 34 are preferably constructed as an extension of other elements of the diaper such as the backsheet 26 or the topsheet 24, preferably both the backsheet 26 and the topsheet 24.

The elasticized waist features 34 may be constructed in a number of different configurations including those described in U.S. Pat. No. 4,515,595 issued to Kievit, et al. on May 7, 1985 and the above referenced U.S. Pat. No. 5,151,092, each of these references being incorporated herein by reference.

The diaper 20 also comprises a fastening system 36 which forms a side closure which maintains the first waist region 56 and the second waist region 58 in an overlapping configuration such that lateral tensions are maintained around the circumference of the diaper to maintain the diaper on the wearer. The fastening system may take on a number of configurations such as adhesive tape tabs, mechanical closure tape tabs, fixed position fasteners, or any other means for tensioning the elasticized waist feature as are known in the art. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No.B1 4,662,875 entitled "Absorbent Article" issued to Hirotsu, et al. on May 5, 1987; and the hereinbefore referenced U.S. Pat. No. 5,151,092; each of which is incorporated herein by reference. In a preferred embodiment, the fastening system comprises a dual tension fastening system such as disclosed in the hereinbefore referenced U.S. Pat. No. 5,151,092.

In a preferred embodiment, the diaper also comprises elasticized side panels 30 disposed in the second waist region 58. (As used herein, the term "disposed" is used to mean that an element(s) of the diaper is formed (joined and positioned) in a particular place or position as a unitary structure with other elements of the diaper or as a separate element joined to another element of the diaper.) The elasticized side panels 30 provide an elastically extensible feature that provides a more comfortable and contouring fit by initially conformably fitting the diaper to the wearer and sustaining this fit throughout the time of wear well past when the diaper has been loaded with exudates since the elasticized side panels allow the sides of the diaper to expand and contract. The elasticized side panels 30 further provide more effective application of the diaper 20 since even if the diaperer pulls one elasticized side panel 30 farther than the other during application (asymmetrically), the diaper 20 will "self-adjust" during wear. While the diaper 20 of the present invention preferably has the elasticized side panels 30 disposed in the second waist region 58; alternatively, the diaper 20 may be provided with elasticized side panels 30 disposed in the first waist region 56 or in both the first waist region 56 and the second waist region 58.

While the elasticized side panels 30 may be constructed in a number of configurations, examples of diapers with elasticized side panels positioned in the ears (ear flaps) of the diaper are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and the hereinbefore referenced U.S. Pat. No. 5,151,092; each of which are incorporated herein by reference. Preferably, each elasticized side panel 30 comprises ear flaps and an elastic side panel member operatively associated therewith, such as disclosed in the above referenced U.S. Pat. No. 5,151,092.

The diaper 20 is preferably applied to a wearer by positioning one of the waist regions, preferably the second waist region 58, under the wearer's back and drawing the remainder of the diaper between the wearer's legs so that the other waist region, preferably the first waist region 56, is positioned across the front of the wearer. The diaperer then wraps the elasticized side panel around the wearer, generally while grasping at least a portion of the fastening system 36. The elasticized side panels will typically be extended and tensioned during this operation so as to conform to the size and shape of the wearer. The fastening system is secured (generally at or to the outer surface 52 of the diaper) to effect a side closure.

Figure 4:
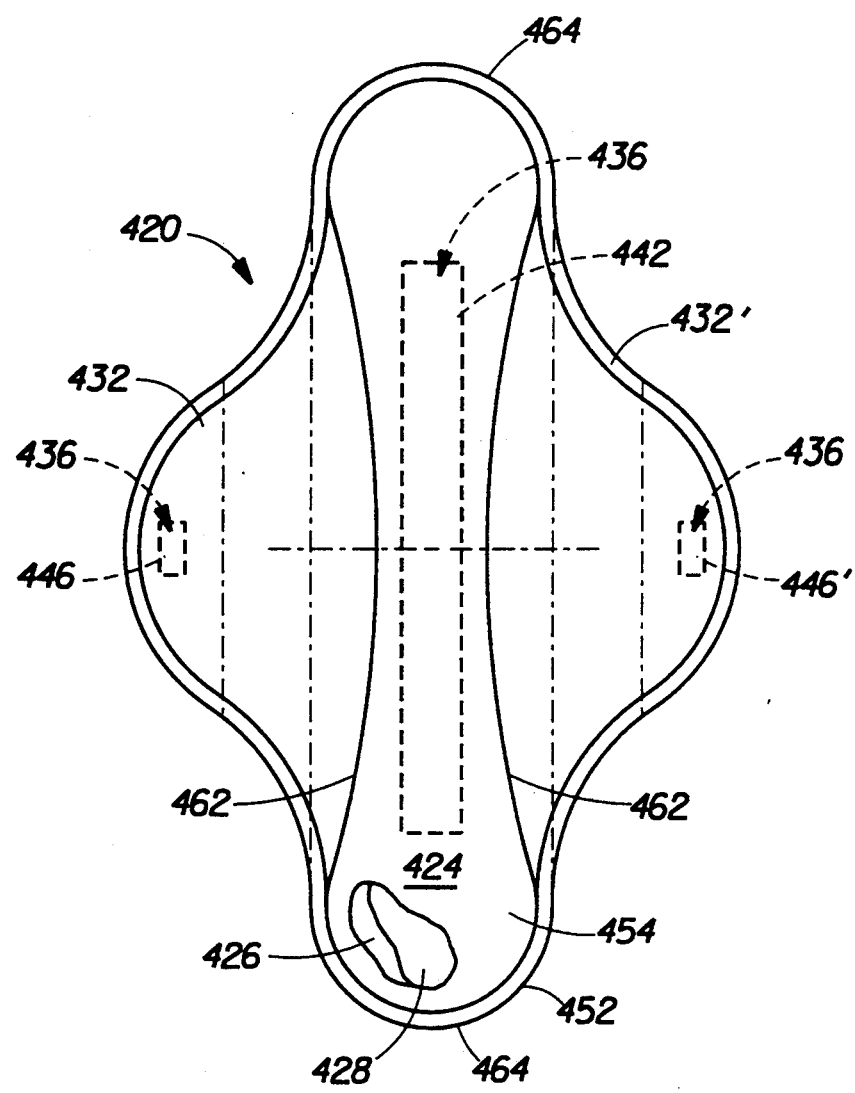
FIG. 4 is a partially cut-away plan view of a sanitary napkin embodiment of the present invention.

Another preferred embodiment of a unitary disposable absorbent article of the present invention is the catamenial pad, sanitary napkin 420, shown in FIG. 4. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia.

FIG. 4 is a Plan view of a sanitary napkin 420 embodying the present invention prior to it being placed in the undergarment of the wearer. As shown in FIG. 4, a preferred sanitary napkin construction comprises a liquid pervious topsheet 424, an absorbent core 428, a liquid impervious backsheet 426, and a fastening system 436 for securing the sanitary napkin to the undergarment of the wearer. While the topsheet 424, the absorbent core 428, and the backsheet 426 may be assembled in a variety of well-known configurations, a preferred sanitary napkin configuration is shown and described generally in U.S. Pat. No. 4,687,478 entitled "Shaped Sanitary Napkin With Flaps" issued to Van Tilburg on Aug. 18, 1987, wherein the sanitary napkin 420 additionally has flaps 432 and 432'. Other preferred sanitary napkin configurations are described generally in U.S. Pat. No. 4,950,264 entitled "Thin, Flexible Sanitary Napkin" issued to Osborn on Aug. 21, 1990; U.S. Pat. No. 4,589,876 entitled "Sanitary Napkin" issued to Van Tilburg on May 20, 1986,; U.S. Pat. No. 4,425,130 entitled "Compound Sanitary Napkin" issued to DesMarais on Jan. 10, 1984; and U.S. Pat. No. 4,321,924 entitled "Bordered Disposable Absorbent Article" issued to Ahr on Mar. 30, 1982. Each of these patents are hereby incorporated herein by reference.

Numerous other sanitary napkin embodiments are disclosed in the literature and could provide configurations for the sanitary napkins herein. For example, suitable configurations are described in PCT International Publication Nos. WO 93/01785 entitled "Stretchable Absorbent Articles," Osborn, et al.; and WO 93/01781 entitled "Curved, Shaped Absorbent Article," Johnson, et al. Both of these references were published on Feb. 4, 1993, and are incorporated herein by reference. Other sanitary napkin embodiments useful herein are disclosed in U.S. Pat. No. 5,009,653 issued to Osborn on Apr. 23, 1991; and U.S. Pat. No. 4,917,697 issued to Osborn, III, et al. on Apr. 17, 1990. In still other alternative embodiments, components or regions of the sanitary napkin may be further structurally modified by folding, bending, corrugating, stacking of layers and affixing of layers to each other. The modifications may be made by including one or more of the structures described in European Patent Application Publication Nos. 0,335,252 and 0,335,253 published in the name of Buell on Oct. 4, 1989; and PCT International Publication No. WO 92/07535 published in the name of Visscher, et al.

FIG. 4 shows a preferred embodiment of the sanitary napkin 420 in which the topsheet 424 and the backsheet 426 are co-extensive and have length and width dimensions generally larger than those of the absorbent core 428 to form the flaps 432 and 432'. The topsheet 424 is joined with and superposed on the backsheet 426 to form the periphery of the sanitary napkin 420. The sanitary napkin 420 has an inside surface 454 and an outside surface 452. In general, the outside surface 452 extends from one end edge 464 to the other end edge 464 and from one longitudinal edge 462 to the other longitudinal edge 462 and is the surface farthest from the wearer during use of the sanitary napkin. When a backsheet 426 is used, it typically forms the outside surface 452. The inside surface 454 is that surface opposite the outside surface 452 and in the embodiment shown is typically formed by the topsheet 424. In general, the inside surface 454 is that surface coextensive with the outside surface 452 and which is for the greater part in contact with the wearer when the sanitary napkin 420 is worn.

In the preferred embodiment of the sanitary napkin 420 as shown in FIG. 4, the fastening system 436 comprises an attachment member 442 comprising adhesive positioned on the outside surface 452 of the sanitary napkin 420 and a release liner (not shown) as is known in the art releasably attached to the adhesive of the attachment member 442.

Since a preferred embodiment of the sanitary napkin 420 of the present invention comprises flaps 432 and 432', the fastening system 436 comprises flap attachment members 446 and 446' comprising adhesive on the flaps 432 and 432' to maintain the flaps 432 and 432' in position after the flaps 432 and 432' have been wrapped around the edge of the crotch portion of the undergarment. A release liner (not shown) is also positioned over each of the flap attachment members 446 and 446' to protect the adhesive until the sanitary napkin 420 is used, the release liner being removed and the flap being wrapped around the edge of the crotch portion of the undergarment.

The topsheet 424 may comprise any of the topsheet materials previously described in reference to the diaper embodiment of the invention. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135 entitled "Absorptive Structures Having Tapered Capillaries" which issued to Thompson on Dec. 30, 1975; U.S. Pat. No. 4,324,246 entitled "Disposable Absorbent Article Having A Stain Resistant Topsheet" which issued to Mullane, et al. on Apr. 13, 1982; U.S. Pat. No. 4,342,314 entitled "Resilient Plastic Web Exhibiting Fiber-Like Properties" which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" which issued to Ahr, et al. on Jul. 31, 1984; and U.S. Pat. No. 5,006,394 entitled "Multilayer Polymeric Film" which issued to Baird on Apr. 9, 1991.

Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE."

The topsheet 424 has two sides (faces or surfaces), including a body-facing side (toward the wearer) and a garment-facing side (core-facing side). The body-facing side of the topsheet 424 generally forms at least a portion of the inside surface 454 of the sanitary napkin 420. In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745 entitled "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. No. 4,950,264 issued to Osborn.

The backsheet 426 may comprise any of the backsheet materials previously described in reference to the diaper embodiment of the invention. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 426 may permit vapors to escape from the absorbent core 428 (i.e., breathable) while still preventing exudates from passing through the backsheet 426.

The absorbent core 428 is positioned between the topsheet 424 and the backsheet 426 and comprises the superabsorbent polymer foams of the present invention. The foams may be incorporated into the absorbent core in the same manner as previously described in reference to the diaper embodiment of the present invention. In a preferred embodiment, the absorbent core 428 comprises the superabsorbent polymer foam formed on an absorbent carrier, more preferably a carrier providing fast wicking properties such as tissue paper, such that the composite absorbent material acts as the absorbent core. The absorbent core preferably comprises a carrier web of fiber material. Suitable fiber materials and cores include those described in reference to the diaper embodiment of the present invention. In a preferred embodiment, the absorbent core is formed by air-laying a substantially dry mixture of fibers, densifying the resultant web if desired or necessary, and then forming the superabsorbent foam on the web.

In a preferred embodiment of the present invention, an acquisition layer may be positioned between the topsheet 424 and the absorbent core 428. The acquisition layer may serve several functions including improving wicking of exudates over and into the absorbent core 428. There are several reasons why the improved wicking of exudates is important, including providing a more even distribution of the exudates throughout the absorbent core 428 and allowing the sanitary napkin 420 to be made relatively thin. (The wicking referred to herein may encompass the transportation of liquids in one, two or all directions (i.e., in the x-y plane and/or in the z-direction)). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials.

In use, the sanitary napkin 420 is secured on the inside of the crotch portion of an undergarment with the pressure-sensitive adhesive fastener side of the sanitary napkin 420 toward the crotch portion of the undergarment. Thus, the undergarment serves as the landing member for the fastening system 436. The release liner is removed from the attachment member 442 and the sanitary napkin 420 is secured in position by pressing the exposed pressure-sensitive adhesive fastener 442 firmly against the crotch material of the undergarment. The release liner is removed from the flap attachment members 446 and 446' to expose the adhesive. The flaps 432 and 432' are then folded under the crotch material of the undergarment and secured in position by pressing the exposed adhesive fastener 446 and 446' firmly against the crotch material of the undergarment, to form a double wall barrier.

TEST METHODS

In describing the present invention, a number of fluid handling, structural and mechanical characteristics of the superabsorbent foams are set forth. In some instances, procedures for determining and measuring certain of these characteristics are described above or are referenced from other patents or publications. In the remaining instances, such characteristics can be determined and measured using the following test fluids and test methods.

In each of the test methods, it is important that the foam sample to be tested has essentially the same morphology of the foam sample as originally formed. Thus, the foam materials should be tested without any preliminary mechanical treatment which is likely to disturb the morphology, e.g., such as sieving or grinding. Where it is necessary or desired to use a cut piece of foam, efforts should be made to avoid edge densification such as described in reference to flexibility testing.

1) TEST FLUIDS—SYNTHETIC URINE

The synthetic-urine utilized in the following tests is a salt solution in distilled water with the surface tension of the solution adjusted to 45 dynes/cm with about 0.0025% of an octylphenoxy polyethoxy ethanol surfactant (Triton X-100, from Rohm and Haas Co.). Such a synthetic urine solution comprises 15 parts of 1% Triton X-100, 60 parts NaCl, 1.8 parts of $CaCl_2.2H_2O$, 3.6 parts of $MgCl_2.6H_2O$ and 6000 parts of distilled water.

2) DETERMINATION OF ABSORBENCY CHARACTERISTICS

A) ABSORPTIVE CAPACITY AND RATE/'TEA BAG" TEST

Absorptive Capacity and Rate can be determined by a gravimetric analytical technique using Synthetic Urine as the fluid for which Absorptive Capacity and Rate of the foam is to be calculated. A sample of superabsorbent polymer foam is placed within a tea bag, immersed in an excess of Synthetic Urine for a specified period of time, and then centrifuged for a specific period of time. The ratio of superabsorbent polymer foam final weight after centrifuging minus initial weight (net fluid gain) to initial weight determines the Absorptive Capacity. Rate can be calculated from the Absorptive Capacity as a function of time.

The following procedure is conducted under standard laboratory conditions at 23° C. (73° F.) and 50% relative humidity. Using a 6 cm ×23 cm cutting die, the tea bag material is cut, folded in half lengthwise and sealed along two sides with a T-bar sealer to produce a 6 cm ×6 cm tea bag square. The tea bag material utilized is a grade 1234 heat sealable material, obtainable from C. H. Dexter, Division of the Dexter Corp., Windsor Locks, Conn., U.S.A., or equivalent. Lower porosity tea bag material should be used if required to retain fine particles of foam material. 0.200 grams plus or minus 0.005 grams of the superabsorbent polymer foam material is weighed onto a weighing paper and transferred into the tea bag and the top (open end) of the tea bag is sealed. An empty tea bag is sealed at the top and is used as a blank. Approximately 300 milliliters of Synthetic Urine are poured into a 1,000 milliliter beaker. The blank tea bag is submerged in the Synthetic Urine. The tea bag containing the superabsorbent polymer foam material (the sample tea bag) is held horizontally to distribute the material evenly throughout the tea bag. The tea bag is laid on the surface of the Synthetic Urine. The tea bag is allowed to wet, for a period of no more than one minute, and then is fully submerged and soaked for 60 minutes. Approximately 2 minutes after the first sample is submerged, a second set of tea bags, prepared identically to the first set of blank and sample tea bags, is submerged and soaked for 60 minutes in the same manner as the first set. After the prescribed soak time has elapsed, for each set of tea bag samples, the tea bags are promptly removed (using tongs) from the Synthetic Urine. The samples are then centrifuged as described below. The centrifuge used is a Delux Dynac II Centrifuge, Fisher Model No. 05-100-26, obtainable from the Fisher Scientific Co. of Pittsburgh, Pa., or equivalent. The centrifuge should be equipped with a direct read tachometer and an electric brake. The centrifuge is further equipped with a cylindrical insert basket having an approximately 2.5 inch (6.35 cm) high outer wall with an 8.435 inch (21.425 cm) outer diameter, a 7.935 inch (20.155 cm) inside diameter, and 9 rows each of approximately 106 3/32 inch (0.238 cm) diameter circular holes equally spaced around the circumference of the outer wall, and having a basket floor with six ¼ inch (0.635 cm) diameter circular drainage holes equally spaced around the circumference of the basket floor at a distance of ½ inch (1.27 cm) from the interior surface of the outer wall to the center of the drainage holes, or an equivalent. The basket is mounted in the centrifuge so as to rotate, as well as brake, in unison with the centrifuge. The sample tea bags are positioned in the centrifuge basket with a folded end of the tea bag in the direction of the centrifuge spin to absorb the initial force. The blank tea bags are placed to either side of the corresponding sample tea bags. The sample tea bag of the second set must be placed opposite the sample tea bag of the first set; and the blank tea bag of the second set opposite the blank tea bag of the first set, to balance the centrifuge. The centrifuge is started and allowed to ramp up quickly to a stable speed of 1,500 rpm, a timer is set for 3 minutes. After 3 minutes, the centrifuge is turned off and the brake is applied. The first sample tea bag and the first blank tea bag are removed and weighed separately. The procedure is repeated for the second sample tea bag and the second blank tea bag.

The absorptive capacity (AC) for each of the samples is calculated as follows:

AC=(sample tea bag weight after centrifuge minus blank tea bag weight after centrifuge minus superabsorbent polymer foam weight)/(dry superabsorbent polymer foam weight).

The Absorptive Capacity value for use herein is the average absorptive capacity of the two samples.

The Absorptive Rate (AR) can be calculated as follows:

AR=(AC for a given sample)/(time of sample submersion)

For example, 10 sets of samples and blanks are prepared and soaked/submerged as for the Absorptive Capacity test, except that one set of sample and blank is removed at one minute intervals and spun as for the Absorptive Capacity test. The Absorptive Capacity and Absorptive Rate is then calculated at various time intervals as desired, as described above.

B) ABSORPTIVE CAPACITY AND RATE/BLUE DEXTRIN TEST

Absorptive capacity in terms of grams of synthetic urine absorbed per gram of superabsorbent polymer foam is determined by swelling the foam samples in several aliquots of Synthetic Urine. The amount of such Synthetic Urine actually absorbed by the foam is determined by a procedure which involves use of a Synthetic Urine solution containing Blue Dextrin so that optical absorbence measurements can be used to calculate the amount of Synthetic Urine that is not taken up by the foam.

(a) Blue Dextrin Solution Preparation

A 0.03% Blue Dextrin (BD) solution is prepared by dissolving 0.3 parts of Blue Dextrin (Sigma D-5751) in 1000 parts of Synthetic Urine (SU) solution. The resulting solution has an absorbence of about 0.25 at its absorbence maximum of 617 nm.

(b) Foam Equilibration

Aliquots of the superabsorbent polymer foam to be tested are swelled in: (i) 20 parts of Synthetic Urine (SU) solution and (ii) 20 parts of Blue Dextrin (BD) solution. The suspension in the Blue Dextrin (BD) solution is prepared in duplicate. In most instances, 0.1–0.2 parts of dry foam material (to 20 parts SU or BD) is required to give a sufficiently high spectrophotometer reading relative to the Blue Dextrin reference solution. One hour of equilibration at ambient temperature under gentle stir-bar stirring is sufficient for swelling equilibrium to be attained. After equilibration, a >3 ml aliquot of supernatant is separated from each suspension by decantation followed by centrifugation.

(c) Absorptive Capacity Determination

The optical absorbency (ABS) of each supernatant is determined spectrophotometrically with an accuracy of 0.001 absorbence unit. The Synthetic Urine solution is used as an ABS=0.0 reference. The absorbency of the supernatant from the Synthetic Urine suspension without Blue Dextrin should not exceed 0.01 absorbence unit; higher values indicate scattering from residual foam particles or residual additives, and further centrifugation is necessary. The absorbency of the Blue Dextrin supernatants should exceed the absorbency of the Blue Dextrin reference solution by at least 0.1 absorbence unit. Absorbency values below this range indicate the need to adjust the amount of superabsorbent polymer foam used to prepare the suspension.

(d) Absorptive Capacity Calculation

The Absorptive Capacity of the superabsorbent polymer foam in gms/gm is calculated from (i) the weight fraction of the foam in the suspension and (ii) the ratio of the excluded volume to the total volume of the suspension. Since Blue Dextrin is excluded from the foam due to its high molecular weight, this ratio is related to the measured absorbencies. The following equation is used to calculate the Absorptive Capacity:

$$\text{Absorptive Capacity} = \frac{(\text{gms BD Solution})}{(\text{gms superabsorbent polymer foam})} \times \left[1 - \frac{(ABS \text{ BD Solution})}{(ABS \text{ BD supernatant} - ABS \text{ SU supernatant})}\right]$$

Absorptive Rate (AR) can be determined from the Absorptive Capacity as a function of time in the same manner as for the above Tea Bag Test, i.e., AR=AC/time. For example, the Absorptive Capacity can be determined by testing a number of samples which have been swelled in Synthetic Urine for several time periods, e.g., 1, 3, 5, and 10 minute intervals, from which the Absorptive Rate can be determined. Alternatively, a continuous absorption curve of absorptive capacity versus time of equilibration may be obtained by using a phototrode-type detector for the SU and BD solutions, from which the Absorptive Rate can be determined.

3) BET SURFACE AREA TO UNIT HASS

The specific surface area to unit mass (m²g) of the superabsorbent polymer foam is determined using the Brunauer-Emmet-Teller (BET) gas adsorption method. This method involves adsorbing a monolayer of a gas (Nitrogen ($N_2$)) on a known mass of a superabsorbent polymer foam sample at liquid nitrogen temperatures. The adsorbed $N_2$ is then desorbed by raising the temperature of the sample (thermal desorption) and detected by a thermal conductivity detector (TCD) whose output is connected to an integrating recorder. The peak area of the desorbed $N_2$ is thus known. Replicate desorption peaks are recorded for each sample, the average of which is the signal area (A). After the sample analysis, the instrument response ($A_{cal}$) is determined by injecting known amounts ($V_c$) of Nitrogen gas (99.99%+) into the system and the instrument response is recorded via the integrating recorder. Acal is the average of the several instrument responses obtained upon injecting the known amounts of $N_2$. The A, $A_{cal}$, and $V_c$ values are then used to determine the specific surface area of the sample using the multi-point BET calculation.

The specific equipment used for these analyses is obtainable from the Quantachrome Corporation (Syosset, N.Y.) and consists of the Quantector Outgassing Station, the Flow Controller, and the Quantasorb Jr. Sample Analysis Unit. These instruments are used as described in the operating manuals for the Quantasorb Junior ® Sorption System, 2/1985, incorporated herein by reference. Various specific $N_2$-Helium mixtures obtained by mixing pure $N_2$ and pure helium via the Flow Controller are used as the adsorbate gas.

0.75 grams ±0.05 grams of foam sample is weighed into the glass sample cell (about 2.5 ml) of the apparatus. The glass cell containing the sample is then placed into the gas flow of the instrument. The samples are outgassed with a 30 ml/min Helium flow using the Quantector for a time sufficient to remove any gases other than Helium from the sample, typically a minimum of 4 hours. After outgassing, the gas flow is changed to a specific $N_2$-Helium gas mixture. The glass sample cell is immersed in liquid Nitrogen and allowed to reach equilibrium. An adsorption curve is generated. The adsorbed $N_2$ is then desorbed by removing the liquid Nitrogen and immersing the glass vial in warm tap water. The adsorbed $N_2$ generates a desorption curve and a peak value (used to calculate the signal area (A)). Adsorption/desorption measurements are performed on each sample using different $N_2$-Helium gas mixtures.

The specific surface area $S_g$ is calculated as follows:

$$S_g = S_t/W;$$

wherein W is the weight of the sample and $S_t$ equals $X_m(6.02 \times 10^{23})A_{cs}$; wherein $A_{cs}$ is the adsorbate cross sectional area. For $N_2$, $S_t$ becomes $X_m(3.483 \times 10^3)m^2$; wherein $X_m$ equals $1/(S+I)$. S is the slope and I is the Y-intercept of the plot of $1/X[(P_o/P)-1]$ versus $P/P_o$.

In calculating the x and y values for the above plot, X equals $(A)X_c/(A)_{cal}$. A is the signal area; $A_{cal}$ is the calibration area; and $X_c$ equals $P_a M_a V_c/6.235 \times 10^4$ T. $P_a$ is the ambient pressure; $M_a$ is the molecular weight of the adsorbate which for $N_2$ becomes 28.0134; $V_c$ is the calibration volume; and T is the ambient temperature in °K. P is the partial pressure of the absorbate; and $P_o$, the saturated vapor pressure, equals $P_g + P_a$; wherein $P_g$ is the vapor pressure (above ambient) and $P_a$ is the ambient pressure.

4) DETERMINATION OF FLEXIBILITY

Foam flexibility can be quantified by referencing a test procedure which is a modification of the ASTM D 3574-86 test used to determine flexibility of cellular organic polymeric foam products. Such a modified test utilizes a foam sample which is 7 cm ×0.8 cm ×0.8 cm and which has been saturated to its absorbent capacity (i.e., soaked in Synthetic Urine for about 15 minutes) with Synthetic Urine at 37° C. The Synthetic Urine-saturated foam strip is bent around a 0.8 cm diameter cylindrical mandrel at a uniform rate of 1 lap in 5 seconds until the ends of the strip meet. The foam is considered flexible if it does not tear or break during this test, i.e., if it passes one bending cycle.

It is important that the cutting process used to make the foam samples does not introduce edge defects in the foam strip. The foam strips of the requisite size should be cut from larger blocks of the same material using a sharp reciprocating knife saw. Use of this or an equivalent type of sharp cutting device serves to substantially eliminate sample edge flaws and edge densification effects which could have adverse impact on the accuracy of certain of the measurements made in carrying out the test procedure. In addition, caliper or thickness measurements should be made when the absorbent structure sample is under a confining pressure of 0.05 psi (350 Pa).

5) EXTRACTABLE LEVELS DETERMINATION (I.E., INSOLUBLES CONTENT)

The solubility/insolubility of a particular component, material, etc. (hereinafter "sample") in the solvent is determined by determining the extractability of the component or material in the solvent at ambient temperature (about 22° C.). Extractability is determined by a gravimetric procedure wherein the sample to be tested is mixed with the solvent, the mixture is filtered, and the weight of the resultant residue is determined.

Into a 500 ml Erlenmeyer flask is weighed accurately (to ±0.1 mg) about 0.25 grams of the sample to be tested (Ws). 250 ml of the solvent is added, and the mixture is stirred slowly for 1 hour. After this hour has passed, stirring is stopped and the mixture is filtered using an Erlenmeyer flask fitted with a pre-weighed 0.45 micron filter paper. The tare weight of the filter is (Wp). After filtration, the filter paper with residue is removed from the funnel and dried in a 120° C. oven for 1 hour. The filter paper is cooled and reweighed to obtain (Wr). (Wr)–(Wp) equals the weight of the residue (r).

Along with the sample, a second flask containing 250 ml of the solvent is stirred and filtered and the filter paper is dried as for the sample in order to obtain a blank weight (Wb). The blank filter paper is pre-weighed (Wbf). Wb–Wbf equals the blank residue (br). The adjusted sample residue (ar) equals (r)–(br).

The level of extractables equals $[(ar)/(Ws)] \times 100$.

EXAMPLE I

A superabsorbent polymer foam may be formed as follows: Approximately 250 grams of aqueous (50% by weight) acrylic acid are 75% neutralized to sodium acrylate using 0.1N NaOH. To avoid the formation of polyacrylic acid, the neutralization is performed by gradually adding the NaOH to the acrylic acid solution with gentle mixing and cooling (with dry ice).

A reaction mixture is prepared as follows:

200 grams of the above prepared aqueous sodium acrylate solution; 0.50 grams N,N'-methylbisacrylamide; 1.3 grams V-50 (2,2'-azobis(2-amidinopropane) dihydrochloride, available from Wako Chemicals USA, Inc.); and 20 grams PEG-600 (polyethylene glycol having a weight average molecular weight of about 600, available from the Union Carbide Co. of Danbury, Conn.) are added to a 1 liter glass reactor fitted with temperature and pressure controls and a high shear mixing apparatus (e.g., an "Ultra Turray" mixer, available from the Tekmar Company of Cincinnati, Ohio). The reactor is at ambient temperature (about 22° C.) and pressure (about 1 atm). A mixture of 60 grams of Freon 1,1,2 (1,1,2-trichlorotrifluoroethane, available from Aldrich Chemical of Milwaukee, Wis.); 3.5 grams SPAN ®20 (sorbitan monolaurate, available from Aldrich Chemical); and 6.5 grams TWEEN ®20 (ethoxylated sorbitan monolaurate, available from Aldrich Chemical) is then added to the reactor. This latter mixture is prepared in advance by adding the components to a reactor similar to the one described above and mixing well.

The reaction mixture is mixed at about 850 rpm for about 10 minutes to stably disperse the Freon 1,1,2. The mixing apparatus is then removed from the dispersion. A foam product is formed by increasing the reactor temperature to 60° C. and maintaining the temperature at 60° C. for about 1 hour; followed by increasing the temperature to 80° C. and maintaining it at 80° C. for about 30 minutes; followed by increasing the temperature to 120° C. and maintaining it at 120° C. for about 30 minutes. The reactor is then cooled to about ambient temperature (about 22° C.).

A mixture of 5 grams of glycerol and 25 grams of isopropyl alcohol is added to the foam in the reactor to impregnate the foam with the mixture. The temperature of the reactor is then increased to and maintained at 180° C. for about 1 hour. The reactor is cooled to ambient temperature (about 22° C.), after which the foam is removed from the reactor and openly placed in a humidified room (80% relative humidity) for 6 hours.

An open-celled superabsorbent polymer foam so formed would have the following properties: a gel volume (i.e., absorptive capacity) of 50 g/g; a swelling rate (i.e., absorptive rate) of 2.8 g/g/sec; an average cell size of 30 microns with a standard deviation of ±16 microns; and a surface area to mass ratio of 0.48 m²/g.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent member comprising:
   (i) a wicking web; and
   (ii) a superabsorbent polymer foam disposed on said wicking web;
   said superabsorbent polymer foam comprising a plurality of mutually connected struts of superabsorbent polymer material to form open cells, said foam having:
   (a) a surface area to mass ratio of at least about 0.2 m²/g;
   (b) an average cell size of less than about 100 microns; and
   (c) a density of less than about 0.5 g/cm³.

2. The absorbent member of claim 1 wherein said superabsorbent polymer foam has an average cell size of less than about 50 microns.

3. The absorbent member of claim 2 wherein the superabsorbent polymer foam has a cell distribution value of from about 1 to about 3.

4. The absorbent member of claim 1 wherein said superabsorbent polymer material of said foam comprises reactants capable of forming said superabsorbent polymer material, said reactants being capable of being made substantially soluble in a solvent; said reactants being expanded in the presence of (i) said solvent and (ii) a blowing agent which is substantially insoluble in said solvent to form an expanded structure; said reactants being reacted to form a superabsorbent polymer material which is substantially insoluble in said solvent.

5. The absorbent member of claim 4 wherein said reactants comprise:
   (a) a substantially water-soluble, unsaturated monomer comprising neutralized carboxyl groups; and
   (b) a substantially water-soluble internal crosslinking agent which is capable of reacting with said monomer to form a substantially water-insoluble polymer material; said internal crosslinking agent being selected from the group consisting of compounds having at least two polymerizable double bonds compounds having at least one polymerizable double bond and at least one functional group reactive with said monomer, compounds having at least two functional groups reactive with said monomer, polyvalent metal compounds which can form ionic linkages, and mixtures thereof.

6. The absorbent member of claim 5 wherein said internal crosslinking agent is expanded and reacted with said monomer in the presence of a surfactant, an initiator, a viscosity control agent, or mixtures thereof.

7. The absorbent member of claim 6 wherein the superabsorbent polymer foam is flexibilized by a plasticizer.

8. The absorbent member of claim 6 wherein said superabsorbent polymer material additionally comprises an external crosslinking agent.

9. The absorbent member of claim 6 wherein
   (a) said monomer is selected from the group consisting of partially neutralized acrylic acid, maleic acid, methacrylic acid, fumaric acid, itaconic acid, maleic anhydride, ethylacrylate, butylacrylate, and mixtures thereof;
   (b) said internal crosslinking agent is selected from the group consisting of N,N'-methylenebisacrylamide, triallylamine, triallylphosphate, and di-or poly-glycidyl ethers of aliphatic polyvalent alcohols;
   (c) said solvent is selected from the group consisting of water, lower alcohols, or mixtures thereof; and
   (d) said blowing agent comprises a substantially water-insoluble compound having a vaporization temperature of less than about 50° C.

10. The absorbent member of claim 1 wherein said superabsorbent polymer foam is formed on said wicking web.

11. The absorbent member of claim 10 wherein said superabsorbent polymer foam is formed on said wicking web in a discontinuous pattern.

12. The absorbent member of claim 11 wherein said wicking web comprises cellulosic fibers.

* * * * *